United States Patent
Wakamiya

(10) Patent No.: US 6,787,639 B1
(45) Date of Patent: Sep. 7, 2004

(54) COLLECTIN

(75) Inventor: Nobutaka Wakamiya, Osaka (JP)

(73) Assignee: FUSO Pharmaceutical Industries, Ltd., Osaka (JP)

(*) Notice: Subject to any disclaimer, the term of this patent is extended or adjusted under 35 U.S.C. 154(b) by 0 days.

(21) Appl. No.: 09/600,932

(22) PCT Filed: Jul. 24, 1998

(86) PCT No.: PCT/JP98/03328

§ 371 (c)(1),
(2), (4) Date: Sep. 8, 2000

(87) PCT Pub. No.: WO99/37767

PCT Pub. Date: Jul. 29, 1999

(51) Int. Cl.[7] ............ C07K 1/00; C07K 14/00; C07H 21/04

(52) U.S. Cl. ............ 530/396; 530/350; 530/395; 536/23.1; 536/23.5; 536/24.3; 536/24.33

(58) Field of Search ............... 530/350, 395, 530/396; 536/23.1, 23.5, 24.3

(56) References Cited

U.S. PATENT DOCUMENTS 5,270,199 A 12/1993 Ezekowitz ............... 435/240.2

FOREIGN PATENT DOCUMENTS

WO  WO 8901519  2/1989

OTHER PUBLICATIONS

Hoppe et al. (1994) Protein Science 3: 1143 1158.*
GenBank (1999) Accession No. AB002631. (Ohtani et al.) Direct submission in 1997.*
Ohtani et al. (1999) J. Biol. Chem. 274(19): 13681–13689.*
Tan et al., "Improvements on the Purification of Mannan–Binding Lectin and Demonstration of its $Ca^{2+}$–Independent Association with a C1s–Like Serine Protease," *Biochem. J.* 391:329–332 (1996).
Epstein, et. al., "The collectins in innate community," *Current Opinion in Immunology*, 8:29–35 (1996).
Ezekowitz, R. A. B. et al., "A Human Mannose–binding Protein is an Acute–phase Reactant that Shares Sequence Homology with Other Vertebrate Lectins," *J. Exp. Med.*, 167:1034–1046 (Mar., 1988).
Ezekowitz, R. A. B. et al., "Mannose–binding protein and susceptibility to chronic hepatitis B infection," *The Lancet*, 348: 1396–1397 (Nov., 1996).
Sastry, K. et al., "The Human Mannose–binding Protein Gene: Exon Structure Reveals its Evolutionary Relationship to a Human Pulmonary Surfactant Gene and Localization to Chromosome 10," *J. Exp. Med.*, 170:1175–1189 (Oct., 1989).

(List continued on next page.)

*Primary Examiner*—Karen Cochrane Carlson
*Assistant Examiner*—Rita Mitra
(74) *Attorney, Agent, or Firm*—Marshall, Gerstein & Borun LLP

(57) ABSTRACT

A gene encoding a novel collectin protein which is expected to exhibit an antibacterial activity, an antiviral activity, etc. particularly in the human body, and its amino acid sequence.

13 Claims, 11 Drawing Sheets

OTHER PUBLICATIONS

Sumiya, et. al., "Molecular basis of opsonic defect in immunodeficient children," *Lancet*, 337: 1569–1570 (Jun., 1991).

Sumiya, et. al., "Mannose–binding protein, genetic variants and the risk of infection," *Q. J. Med.*, 89: 723–726 (1996).

Super, et. al., "Association of Low Levels of Mannan–binding Protein with a Common Defect of Opsonisation," *Lancet*, 2: 1236–1239 (Nov., 1989).

Suzuki et al., "Cloning and Sequencing of a cDNA Coding for Bovine Conglutinin," *Biochem Biophys Res Commun*, 191/2, 335–342 (1993).

Suzuki, et al., "Characterization of Recombinant Bovine Congulutinin Expressed in a Mammalian Cell," *Biochem. Biophys. Res. Commun.*, 238: 856–863 (1997).

Taylor, M. E. et al., "Structure and evolutionary origin of the gene encoding a human serum mannose–binding protein," *Biochem J.*, 262: 763–771 (1989).

Thomas, et al., "Mutation of gene for mannose–binding protein associated with chronic hepatitis B viral infection," *Lancet*, 348: 1417–1419 (Nov., 1996).

Wakamiya, N. et. al., "The Mannose Binding Protein and Congulutinin in Bovine Serum Have a Antiviral Activity Against Influenza Virus," *Glycoconjugate Journal*, 8: 235 (1991).

Wakamiya, N. et. al., "Isolation and Characterization of Conglutinin as an Influenza A Virus Inhibitor," *Biochem. Biophys. Res. Comm.*, 187: 1270–1278 (Sep., 1992).

Garred, et al., "Subceptibility to HIV infection and progression of AIDS in relation to variant alleles of mannose–binding lectin," *The Lancet*, 349:236–240 (Jan., 1997).

Kawai, T. et al., "Cloning and characterization of a cDNA encoding bovine mannan–binding protein," *Gene*, 186(2):161–165 (Feb., 1997).

Kurata, H., "Structure and Function of Mannan–Binding Proteins Isolated from Human Liver and Serum," *J. Biochem.*, 115(6):1148–1154 (1994).

Lim, B. L. et al., "Primary Structure of Bovine Collectin–43 (CL–43). Comparison with conglutinin and lung surfactant protein–D," *J. Biol. Chem.*, 269(16):11820–11824 (Apr., 1994).

Lipscombe, R. J. et al., "Mutations in the Human Mannose–Binding Gene: Frequencies in several population groups," *European Journal of Human Genetics*, 4(1): 13–19 (1996).

Lu, et al., "Purification, characterization and cDNA cloning of human lung surfactant protein D," *Biochem. J.*, 284: 795–802 (1992).

Malhortra et al., "Interaction of C1q receptor with lung surfactant protein A*," *Eur. J. Immun.*, 22: 1437–1445 (1992).

Malhortra et al., "Glycosylation changes of IgG associated with rheumatoid arthritis can activate complement via the mannose–binding protein," *Nature Medicine*, 1(3): 237–243 (Mar., 1995).

Nepomuceno, R. R. et al., "cDNA Cloning and Primary Structure Analysis of C1qR($_p$), the Human C1q/MBL/SPA Receptor That Mediates Enhanced Phagocytosis In Vitro," *Immunity*, 6(2):119–129 (Feb., 1997).

* cited by examiner

```
MBP    MSLFPS--LPLLLSMVAASYSETVTCEDAQK------CPAVIACSS----PGINGFPGRDGRDGTKGEKGEPG
SP-A   MWLCPLALTLILMA--------------------ASGAACEVKDVCV---------------------GSPG
SP-D   MLLFLL-SAIMLTQ-PLGYLEAEMKTYSHRTPSACTLVMCSSVESGLPGRDGRDGREGPRGEKGDPG   70

IPGTPGSHGLPGRDGR----------------DGVKGDPGPPGPMGPPG-------ELP
       LPGAAGQAGMPGQAGPVGPKGDNGSVGEPGPPGKGDIGPSGEPGPPGVPGPAGREGPLGKQGNIGPQGKPGP   140

QGLRGLQGP--QPFGNNGLPGAPGVPGE----------RGEXGDPGERGPPGL
       PGKLGPPGNPGPSGSPGPKGQK
       KGEAGPKGEVGAPGMQGSAGARGLAGPKGERGVPGNAGAAGSAGAMGPQGSPGARGPPGLKGDK   210
```

FIG. 2

```
MBP  GDPG-KSPDGDSLAA----------SERKALQTEMARIKKWLTFSLGKQVGNKFFLTNGEIMTFEKV
SP-A  -FAHLDEELQATLHD----FRHQILQTRGALS-LQGSI----------MTVGEKVFSSNGQSITFDAI    280
SP-D  GIPGDKGDKGEPGLPGAKGESLGPDVASLRQQVEALQGQVQHLQAAFSQYKKVELFPNGQSVGEKIFKTAGFVKETEA

KALCVKFQASVATPRNAAENGAIQNLI----KEDAFLGITDEKTEGQFVDLTGNRLTYTNWNEGEPNNAGS
     QEACARAGGRIPAVPRNPEENDAIASFVKKYNTYAYVGLTEGPSPGDFRYSDGTPVNYTNWYRGEPAGRG-   350
     QLLCTQAGGQLASPRSAAENPALQQLVAKNEAAFLSMTDSKTEGKFTYPTGESLVYSNWAPGEPNDDG

DEDCVLLLKNGQWNDVPCSTSHLAVCEFPI*
     KEQCVEMYTDGQWNDRNCLYSRLTICEF*---
     SEDCVEIFTNGKWNDRACGEKRLVVCEF*---

FIG. 3
```

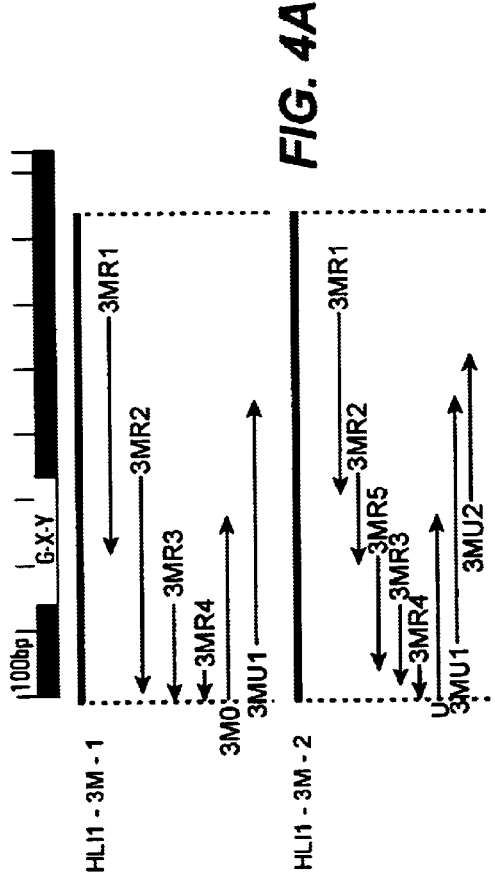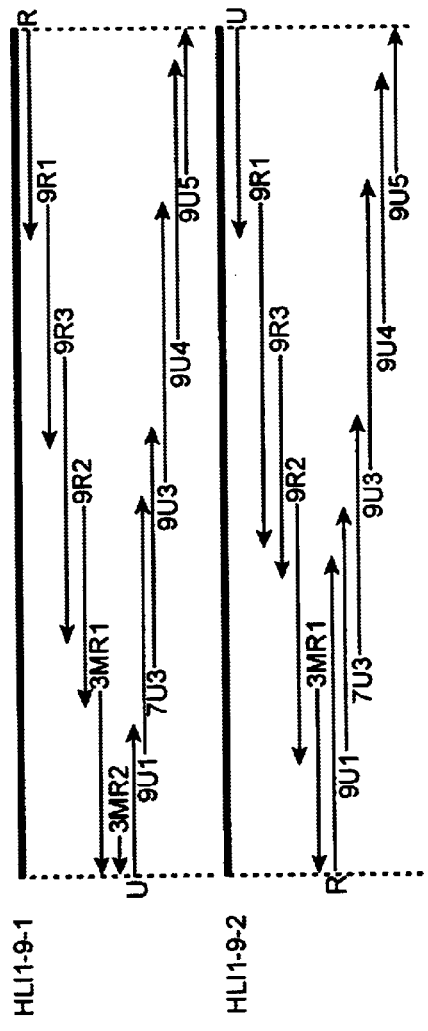

COLLECTIN

This application is a §371 national stage application of PCT/JP98/03328 filed Jul. 24, 1998 which claims priority to Japanese Patent Application No. HEI-10-11281 filed Jan. 23, 1998.

FIELD OF THE INVENTION

The present invention relates to a novel collectin which is useful for investigating mechanisms of biological defense, and is expected to be applied for utilizing as materials for medicines because it may have physiological activities including anti-viral activities and the like.

BACKGROUND ART

Collectin is a generic name of proteins having calcium-dependent carbohydrate recognition domain (CRD) and collagen-like region, and the member of these proteins is conceived to involve in basic immunity systems against a wide spectrum of microorganisms such as bacteria and viruses.

The collectins which have been identified heretofore include mannan-binding protein (MBP, SEQ ID NO: 27), surfactant protein A (SP-A, SEQ ID NO: 28), surfactant protein D (SP-D, SEQ ID NO: 29) and conglutinin. These collectins are known to be constituted from basic structures comprising four unique regions of: (1) calcium-dependent carbohydrate recognition domain (CRD), (2) neck region, (3) collagen-like region and (4) N-terminal region containing cysteine [Malhortra et al., Eur.J.Immunol. Vol.22, 1437–1445, 1992] (see, FIG. 1(a)). A subunit can be formed from the three basic structures through making a triple helix in the collagen-like region, and such subunit constitutes an oligomer, e.g., trimer, tetramer and hexamer.

In vertebrates, mechanisms involving cellular immune responses and specific antibody reactions are considered as dominant host-defense systems against inversion of the pathogenic bacteria, viruses and the like. Recently, involvement in nonspecific immune responses of the lectins such as conglutinin has been suggested, for example, it was reported that the lectins may play important roles in neutralizing and removing the various microorganisms in infants having insufficient maternal antibodies and undeveloped specific defense systems [Super et al., Lancet, Vol.2, 1236–1239, 1989].

Moreover, with respect to the roles of the lectins in the biological host-defense systems, it was reported that the host becomes susceptible to infection by, for example, a reduction of the MBP concentration in blood due to genetic mutation of the MBP gene [Sumiya et al., Lancet, Vol.337, 1569–1570, 1991].

The present inventors have found that the conglutinin and the mannan-binding protein can inhibit infection and hemagglutination activity of H1 and H3 Type Influenza A viruses [Wakamiya et al., Glycoconjugate J., Vol.8, 235, 1991; Wakamiya et al., Biochem. Biophys. Res. Comm., Vol.187, 1270–1278, 1992].

Thereafter, the present inventors isolated a cDNA clone encoding the conglutinin, and found that closer correlation may exist between the conglutinin gene and various surfactant protein D gene [Suzuki et al., Biochem. Biophys. Res. Comm., Vol.191, 335–342, 1993].

As described above, the collectin has been expected to be useful in investigating mechanisms of biological defense, and be applicable for utilizing as materials for medicines, however, the presence of any other molecular species belonging to this protein family has not been elucidated.

DISCLOSURE OF THE INVENTION

The present invention was accomplished in consideration of the aforementioned state of art, and is directed to provide a novel collectin which can be expected to exhibit physiological activities such as anti-bacterial, anti-viral activity, especially in human body.

Accordingly, to provide the following polynucleotide and protein which share characteristic structures of those belonging to the collectin family, and which are distinct from the collectins reported heretofore is intended by the present invention:

[1] A polynucleotide comprising the nucleotide sequence which encodes a protein having the amino acid sequence set out in SEQ ID NO: 2;

[2] A polynucleotide comprising the nucleotide sequence set out in SEQ ID NO: 1;

[3] A polynucleotide which encodes a collectin protein wherein said polynucleotide can hybridize under a stringent condition with a probe produced from a genomic clone which shares high homology to a consensus collectin amino acid sequence set out in SEQ ID NO:3 Glu-Lys-Cys-Val-Glu-Met-Tyr-Thr-Asp-Gly-Lys-Trp-Asn-Asp-Arg-Asn-Cys-Leu-Gln-Ser-Arg-Leu-Ala-Ile-Cys-Glu-Phe;

[4] A polynucleotide which can hybridize with any of the polynucleotide according to any of [1] to [3], wherein the protein encoded by said polynucleotide comprises: (1) $Ca^{2+}$-dependent carbohydrate recognition domain (CRD), (2)neck region. (3) collagen-like region, and (4) N-terminal region containing cysteine;

[5] A collectin protein encoded by the polynucleotide according to any of [3] or [4];

[6] A collectin protein comprising the amino acid sequence set out in SEQ ID NO:2;

[7] A collectin protein comprising the amino acid sequence encoded by the polynucleotide comprising the nucleotide sequence set out in SEQ ID NO: 1;

[8] The collectin protein according to any of [5] to [7], wherein the amino acid sequence of the protein comprises deletion, substitution and/or addition of one or more amino acids, and wherein the protein comprises: (1) $Ca^{2+}$-dependent carbohydrate recognition domain (CRD), (2)neck region, (3) collagen-like region, and (4) N-terminal region containing cysteine.

BRIEF DESCRIPTION OF THE DRAWINGS

FIG. 2 shows the alignment of the preceding half portions of amino acid sequences (SEQ ID NOS: 27–29) of three collectins reported heretofore;

FIG. 3 shows the alignment of the latter half portions of the amino acid sequences (SEQ ID NOS: 27–29) in FIG. 2;

FIG. 4 shows each of the primers used for sequencing the novel collectin polynucleotide of the present invention, and maps of the nucleotide sequence which were read from the sequencer (a, b); and an ORF of the obtained collectin (a);

FIG. 5 shows the alignment of the preceding half portions of amino acid sequences (SEQ ID NOS: 27–29) of the three collectins reported heretofore and the novel collectin of the present invention;

FIG. 6 shows the alignment of the latter half portions of the amino acid sequences (SEQ ID NOS: 27–29) in FIG. 5;

FIG. 9 shows a result of genomic Northern analysis of various human tissues, i.e., (a) heart, (b) brain, (c) placenta, (d) lung, (e) liver, (f) skeletal muscle, (g) kidney and (h) pancreas with the novel collectin of the present invention to clarify the tissue distribution of the collectin;

BEST MODE FOR CARRYING OUT THE INVENTION

Figure 1:
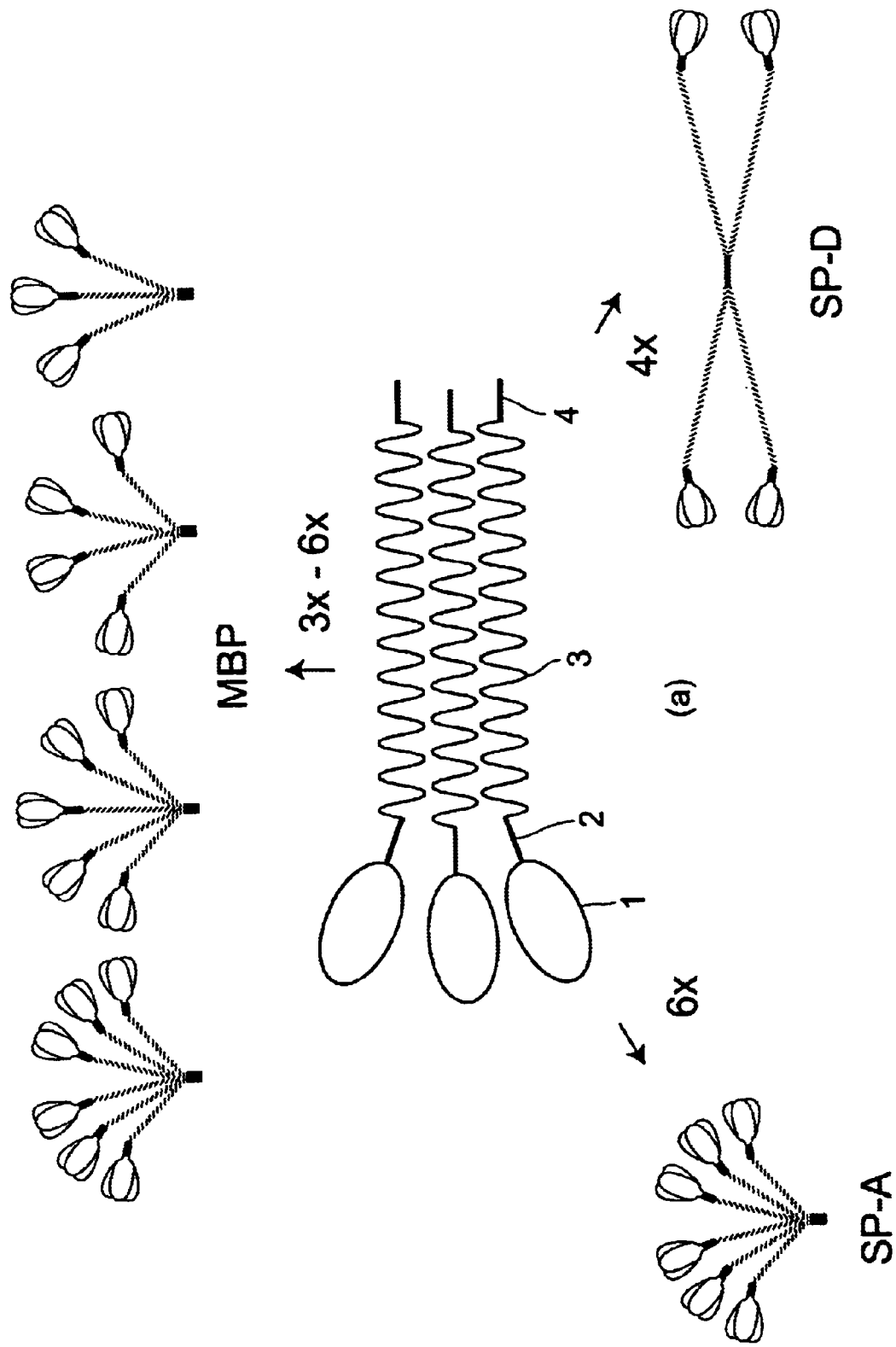
FIG. 1 is a profile showing basic structures and overviews of the principal collectins reported heretofore.

In the preferred embodiment of the present invention, the probe in the above [3] may be amplification products by PCR which was performed using the primers which have the following sequences:

TTTTGATGGAGGCTCCATACC (SEQ ID NO: 7); and

CTGCCAACACACTCATCGCTG (SEQ ID NO: 8).

Thus, desired polynucleotide encoding the collectin protein can be suitably obtained.

Moreover, in the preferred embodiment, the polynucleotide may be cDNA.

Further, the protein of the present invention may preferably consist of the amino acid sequence which is identical to that derived from human, because it can be expected to exhibit physiological activities such as anti-bacterial, anti-viral activity in human body, thereby useful physiologically active material for medicines may be resulted. Therefore, it is intended that the protein of the present invention may be the collectin protein derived from human. We examined various human tissues, and expression of the collectin protein in human liver which seems to be useful could be revealed.

The stringent hybridization condition in the inventions of the above [3] and [4] may include for example, a series of the following steps for the hybridization: prehybridization in a solution of 5×SSC (prepared by diluting 20×SSC (3 M NaCl, 0.3 M sodium citrate)), 1% blocking agent (Boehringer Mannheim), 0.1% N-lauroyl sarcosine, and 0.02% SDS, at 68° C. for an hour; and hybridization in a solution of 5×SSC, 1% blocking agent, 0.1% N-lauroyl sarcosine, and 0.02% SDS containing cDNA probes (10 ng/ml), at 55° C. for 16 hours; washing in a solution of 2×SSC/0.1% SDS for 5 minutes, 2 times; and washing in a solution of 0.5×SSC/0.1% SDS at 55° C. for 15 minutes, 2 times. However, several modifications/alterations of these conditions may be made, based on the knowledge of the skilled art, such as the concentration of the solution, incubation temperature and time.

In addition, the N-terminal region containing cysteine in the above [8] may contain at least one cysteine residue, preferably one cysteine residue.

Further, deletion, substitution and/or addition of one or more amino acids in the above [8] may be those which result in less changes of hydrophilic/hydrophobic nature, acidic/basic nature, and constitutional residues of the collectin proteins, without bringing much alterations of the properties in the above-described four regions, specifically in both of the regions: (1) $Ca^{2+}$-dependent carbohydrate recognition domain (CRD) and (3) collagen-like region. Taking the structural sequences of the proteins belonging to the collectin family reported heretofore into account, for example, deletion, substitution and/or addition of 1–10 amino acid residues in (1) $Ca^{2+}$-dependent carbohydrate recognition domain (CRD) and in (2)neck region, 1–100, preferably 1–15 amino acid residues in (3) collagen-like region, and 1–20 amino acid residues in (4) N-terminal region containing cysteine and the signal sequence may be allowed.

The present invention will be described in more detail by the non-limiting illustrative examples. It is intended that the present invention encompasses all modifications and variations which occur to those skilled in the art upon consideration of the disclosures herein, and in particular those embodiments which are within the broadest proper interpretation of the claims and their requirements.

The Examples illustrate: the search on EST data base (Example 1); preparation of the probes for screening (Example 2); screening of cDNA library derived from human liver (Example 3); sequencing of nucleotide sequence of the novel collectin (Example 4); genomic Southern analysis of the novel collectin (Example 5); Northern analysis of the novel collectin with various human tissues (Example 6); genomic Southern analasis of the novel collectin with tissues from various species of animals (Example 7); and genetic study of the novel collectin (Example 8).

EXAMPLE 1

Search on EST Data Base

Highly conserved regions between molecules of known collectin proteins, i.e., MBP, SP-A and SP-D were searched by comparing the amino acid sequences thereof (see FIGS. 2 and 3, in which amino acid residues which were recognized to be homologous between those proteins were boxed). As a result, it was suggested that the region consisting of 27 amino acids, namely from amino acid 220 to 246 of human MBP sequence (shown in FIG. 3, reversed characters), was highly homologous. Therefore, some consensus sequence, corresponding to this region were prepared, and conducted searches on EST (Expressed Sequence Tags) data base with such sequences. For this search, the EST data base published on Oct. 11, 1996 was employed, which included 676750 sequences.

Consequently, some data comprising homologous amino acid sequences were obtained. Searches on GenBank/EST data base with thus obtained data of the amino acid sequences were further conducted, and deduced whether they were derived from known, or unknown substances. Thereby, it was confirmed that data including highly homologous but unknown nucleotide sequence (registered as: R29493) could be identified when the following amino acid sequence was used as a consensus sequence:

Glu-Lys-Cys-Val-Glu-Met-Tyr-Thr-Asp-Gly-Lys-Trp-Asn-Asp-Arg-Asn-Cys-Leu-Gln-Ser-Arg-Leu-Ala-Ile-Cys-Glu-Phe (SEQ ID NO: 3).

The data contained the sequence of 5'-terminal 326 nucleotides of a clone F1-1006D from human embryonic (22 weeks old) liver cDNA library.

Thereafter, the clone was kindly provided from the owner, Mr. Hee-Sup Shin (Pohang Institute of Science & Technology (Pohang, Korea)). The insert size of the clone was about 600 bp, with the 5'-terminal end being incorporated adjacent to the nucleotide sequence set out in SEQ ID NO: 4, while 3'-terminal end being incorporated into plasmid pSK(−) (pBluescriptIISK(−)) at XhoI restriction site.

EXAMPLE 2

Preparation of the Probes for Screening

The insert of the clone described above in Example 1 was excised using EcoRI and XhoI, then incorporated into pUC18, and sequenced using a primer (Pharmacia, M13, Universal Primer (SEQ ID NO: 5, 5'-fluorescein-CGACGTTGTAAAACGACGGCCAGT-3')) and M13 Reverse Primer (SEQ ID NO: 6, 5'-fluorescein-CAGGAAACAGCTATGAC-3').

In the nucleotide sequence obtained, an open reading frame was selected through matching it to the collectin amino acid sequence. The nucleotide sequence corresponding to the amino acid sequence which could be read from the above open reading frame was picked out, and primers for digoxigenin (DIG) labeled cDNA probes (Reverse Primer (SEQ ID NO: 7) and Forward Primer (SEQ ID NO: 8)) corresponding to the parts of the nucleotide sequences were produced using DNA/RNA Synthesizer (Applied Biosystems, 392A). DIG labeling was achieved using PCR DIG Probe Synthesis Kit (Boehringer Mannheim). The reaction mixture contained: DNA fragments which were the excised inserts from the clone F1-1006D with EcoRI and XhoI (4.4 ng/μl, 12 μl: 52.8 ng), 10× buffer: 5 μl, 25 mM $MgCl_2$: 5 μl, dNTP (PCR Labeling Mix): 2.5 μl, 20 μM Reverse Primer: 2.5 μl, 20 μM Forward Primer: 5 μl, $H_2O$: 18 μl, Taq Polymerase: 0.5 μl. PCR reaction was carried out using Zymoreactor (Atto Corp.,) through 35 cycles of: 1 minute at 92° C., 1 minute at 55° C., and 2 minutes at 72° C.

EXAMPLE 3

Screening of cDNA Library Derived from Human Liver

First, phage cDNA library was titrated as follows. *Escherichia coli* Y1090r⁻ which had been cultured at 37° C. for 16 hours in mLB medium (LB medium (1 g trypton, 0.5 g yeast extract and 0.5 g NaCl in total volume of 100 ml) containing 10 mM $MgSO_4$ and 0.2% maltose), 0.2 ml, and 0.1 ml of cDNA library serially diluted with SM buffer (5.8 g NaCl, 2 g $MgSO_4$.$7H_2O$, 2 M Tris-HCl (pH 7.5) 25 ml, and 2% gelatin 5 ml in total volume of 1 L) were incubated at 37° C. for 15 minutes, then the mixtures were added to 2.5 ml of LB-TOP agar (0.75% agar/LB medium) to make homogenous solutions, and plated onto LB Plates (Iwaki Glass 90 mm φ, 1.5% agar/LB medium). The added solutions were hardened at a room temperature for 15 minutes, then incubated for 5 hours at 42° C. the plaques on each of the plates were counted, and the titer of the phage was calculated. The titer calculated here was $2.3 \times 10^{10}$ pfu/ml.

The screening with thus titrated cDNA library using the probes prepared in Example 2 was conducted as follows. *Escherichia coli* Y1090r⁻ which had been cultured at 37° C. for 6 hours in mLB medium, 0.6 ml and cDNA library diluted with SM buffer, to $1 \times 10^5$ pfu were incubated at 37° C. for 15 minutes, then the mixture was added to 7.5 ml of LB-TOP agar (0.75% agarose) to make a homogenous solution. The solution was plated onto ten LB square plates of 140 mm² (Nissui Seiyaku), hardened at a room temperature for 15 minutes, then the plates were incubated for 5 hours at 42° C. After plaque formation of each of the plates was determined, the transfer to the nylon membranes, using Nytran 13N (Schleicher and Schuell Co.) as a filter was performed. The filters (12.5 cm×9.0 cm in size) were immersed in distilled water for 10 minutes to be wet, then the excess water was removed on Whatmann 3MM Paper. The filters were placed on the plates having the plaques formed thereon. After standing for two minutes, the filters were recovered and air dried for 10 minutes. The phage DNA on the filters was denatured for 2 minutes with 0.2 M NaOH/1.5 M NaCl, followed by neutralization with 0.4 M Tris-HCl (pH7.6)/2×SSC for 2 minutes and washing with 2×SSC for 2 minutes. Thereafter, the DNA was fixed on the membrane by UV irradiation with GS GENE LINKER (BioRad).

Hybridization and detection of the signals were conducted as follows. The filters were soaked in 2×SSC, and the excess water was removed using Whatmann 3MM Paper. Then, the filters were placed in a hybridization bag and prehybridization at 68° C. for one hour in a hybridization solution (5×SSC, 1% blocking agent, 0.1% N-lauroyl sarcosine and 0.02% SDS) was performed. Subsequently, the hybridization solution was removed from the bag, and the hybridization solution containing DIG labeled cDNA probe at a concentration of 10 ng/ml was added thereto, and hybridization was at proceeded at 55° C. for 16 hours. After the hybridization was completed, the filters were washed in a solution of 2×SSC/0.1% SDS at a room temperature for 5 minutes, 2 times; and further washed in a solution of 0.5×SSC/0.1% SDS for 15 minutes at 55° C., 2 times. Then, SDS was removed using DIG buffer I (100 mM Tris-HCl, 150 mM NaCl (pH7.5)) for 1 minute, and the filters were blocked with DIG buffer II (1% blocking agent in DIG buffer I) for 30 minutes. After washing the filters with DIG buffer I for one minute, a solution of alkaline phosphatase labeled anti-DIG antibody (Boehringer Mannheim) which was diluted to 5000-fold in DIG buffer II was added, and the reactions between antigen and antibody were allowed for 30 minutes. The filters were then washed twice with DIG buffer I for 15 minutes at a room temperature. Through the subsequent treatment of the filters with DIG buffer III (100 mM Tris-HCl, 100 mM NaCl (pH 9.5), 50 mM $MgCl_2$) for 3 minutes, the concentration of $Mg^{2+}$ was elevated. Finally, a solution of NBT/BCIP (WAKO Chem., Co.) in DIG buffer III was added for color development, thereby 13 positive clones were identified.

The plaques corresponding to these clones were excised from the plates and placed in the tubes containing 1 ml of SM buffer. After stirring for 10 minutes, each of the buffer solution was serially diluted with SM buffer, and 0.1 ml of the diluted solution was mixed with 0.2 ml cultures of *Escherichia coli* Y1090r⁻ which had been cultured in mLB medium for 16 hours at 37° C. The mixture was incubated for 15 minutes at 37° C., and added to 2.5 ml of LB-TOP agarose to make a homogenous solution. The solution was plated onto ten LB plates (90 mm φ), hardened at a room temperature for 15 minutes, then the plates were incubated for 5 hours at 42° C. With respect to several plaques thus obtained, the secondary screening was performed essentially in accordance with the procedures of the primary screening as described above.

EXAMPLE 4

Sequencing of the Novel Collectin Nucleotide

The plaques from suitable two clones (HLI1-3M and HLI1-9) which were selected from the positive clones obtained in the above secondary screening were excised from the plates, and placed respectively in the tubes containing 1 ml of SM buffer. After stirring, 50 µl of each of the solution was added to 4.95 ml of mLB medium with 50 µl cultures of *Escherichia coli* Y1090r⁻ which had been cultured in mLB medium for 16 hours at 37° C. The mixture was cultured for 16 hours at 37° C., then one drop of chloroform was added thereto. After stirring for 3 minutes, the mixture was subjected to centrifuge at 10,000 rpm for 5 minutes to obtain a supernatant therefrom.

The insert DNA was amplified by PCR with TaKaRa LA PCR Kit Ver.2 (TAKARA Syuzo, Co.) using the resulting supernatant as a template. PCR reactions contained the supernatant, 11 µl, 10×LA PCR Buffer II ($Mg^{2+}$free) 2.5 µl, 25 mM $MgCl_2$: 5 µl, dNTP Mix: 8 µl, 20 µM λ gt11 Reverse Primer (SEQ ID NO: 9: 5'-TTGACACCAGACCAACT GGTAATG-3'): 2.5 µl, 20 µM λ gt11 Forward Primer (SEQ ID NO: 10: 5'-GGTGGCGACGACTCCTGGAGCCCG-3'): 1 µl, LA Taq polymerase: 0.5 µl, and $H_2O$: to make final volume 50 µl. The PCR reaction was performed using Applied Biosystems Gene Amp PCR System 9690, with 30 cycles of: 10 seconds at 98° C., and 5 minutes at 68° C. The PCR product was verified by the electrophoresis with 1% agarose gel, and purified through excising from the gel. For this purification step, Sephaglas BandPrep Kit (Pharmacia) was used.

The excised DNA fragment was incorporated into pCR2.1 vector (Invitrogen, TA Cloning Kit). The recombinant vector was transformed into TOP10F' cell included in the Invitrogen TA Cloning Kit. The transformants were cultured in LB medium (containing 100 µg/ml ampicillin), and two plasmid for each of the clones (HLI1-3M-1, HLI1-3M-2, HLI1-9-1 and HLI1-9-2) were extracted by alkaline SDS method followed by nucleotide sequencing with Autoread Sequencing Kit (Pharmacia) and A.L.F. Autosequencer. M13 Universal Primer (SEQ ID NO: 5) and M13 Reverse Primer (SEQ ID NO: 6) from the Autoread Sequencing Kit were used first, then full length nucleotide sequence was determined based on the resulting elucidated nucleotide sequences using the following primers (3MUO-9R3) which were produced on a DNA/RNA synthesizer and labeled with FITC (Pharmacia, Fluore Prime):

3MU0: 5'-fluorescein-TAATGGTAGCGACCGGCGCT-3' (SEQ ID NO: 11),
3MU1: 5'-fluorescein-AAACCAATTTATACTCCTGG-3' (SEQ ID NO: 12),
3MU2: 5'-fluorescein-AATATTGGCAAGACTGGGCC-3' (SEQ ID NO: 13),
3MR1: 5'-fluorescein-GATGAGTGTGTTGGCAGCAT-3' (SEQ ID NO: 14),
3MR2: 5'-fluorescein-GTATCTTCCACAATCACAGA-3' (SEQ ID NO: 15),
3MR3: 5'-fluorescein-TTAATTCCTTTCGGCCCCAT-3' (SEQ ID NO: 16),
3MR4: 5'-fluorescein-GCAAAAGAAATAGTACCAGG-3' (SEQ ID NO: 17),
3MR5: 5'-fluorescein-CATATCACCCAGTTCTCCTT-3' (SEQ ID NO: 18),
9U1: 5'-fluorescein-AGCAGGGATTAGGGAAACTG-3' (SEQ ID NO: 19),
9U3: 5'-fluorescein-CTGTGAGCGTCATTACAGTT-3' (SEQ ID NO: 20),
9U4: 5'-fluorescein-GGTTGTCTATATGTCAAATG-3' (SEQ ID NO: 21),
9U5: 5'-fluorescein-TATGGCCATGGCTATACTTG-3' (SEQ ID NO: 22),
7U3: 5'-fluorescein-ATCGCTGACTATGTTGCCAA-3' (SEQ ID NO: 23),
9R1: 5'-fluorescein-CAAGTATAGCCATGGCCATA-3' (SEQ ID NO: 24),
9R2: 5'-fluorescein-AACTGTAATGACGCTCACAG-3' (SEQ ID NO: 25), and
9R3: 5'-fluorescein-CATTTGACATATGAACAACC-3' (SEQ ID NO: 26)

As a result, the obtained cDNA clone contained 1295 bases set out in SEQ ID NO: 1, which comprises ORF (open reading frame) of 831 base pairs encoding 277 amino acids as shown in SEQ ID NO: 2.

The outline of this nucleotide sequencing strategy is shown in FIG. 4. An ORF of the obtained collectin is illustrated in FIG. 4(*a*), wherein G—X—Y denotes a collagen-like region. Further, in FIG. 4(*b*), each of the primer names and maps of the nucleotide sequence which were read from the sequencer (shown as allows), as well as M13 Universal Primer (shown as U) and M13 Reverse Primer (shown as R) are illustrated.

Figure 5:
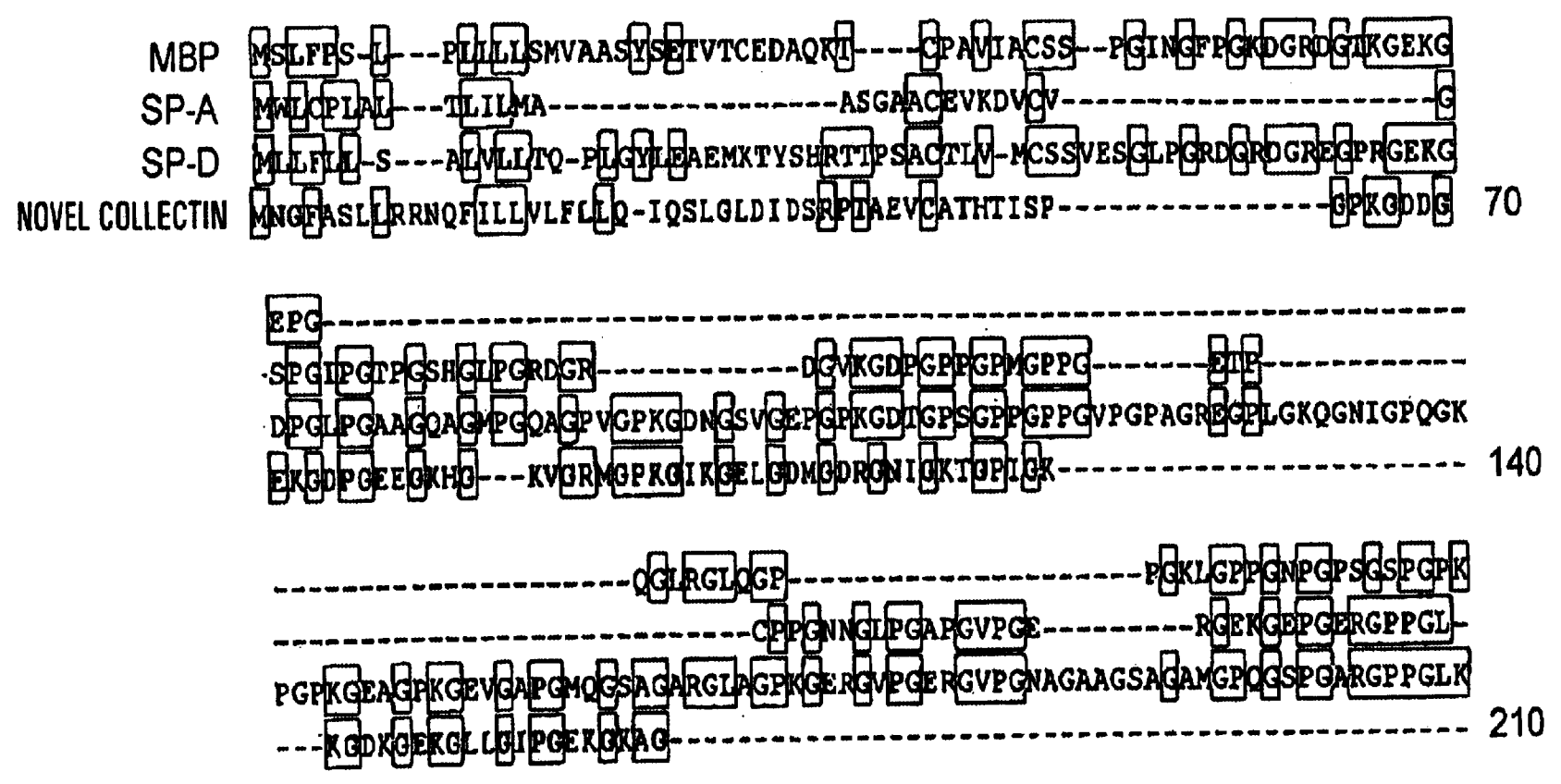
Figure 6:
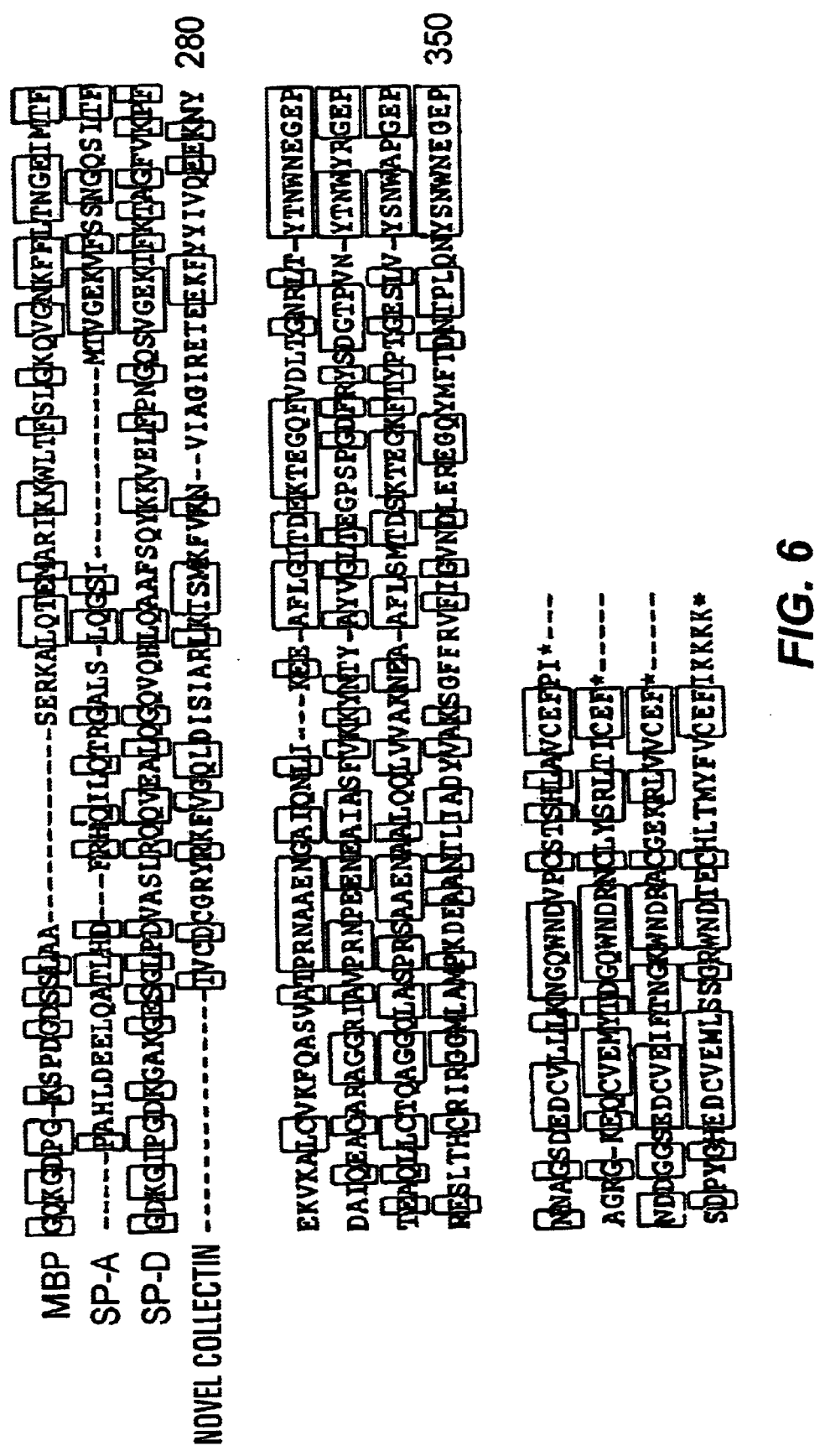

FIGS. 5 and 6 show the alignment of the amino acid sequence of the novel collectin of the present invention and those of three collectin proteins reported heretofore. Similarly to FIGS. 2 and 3, amino acid residues which were recognized to be homologous were boxed.

Figure 7:
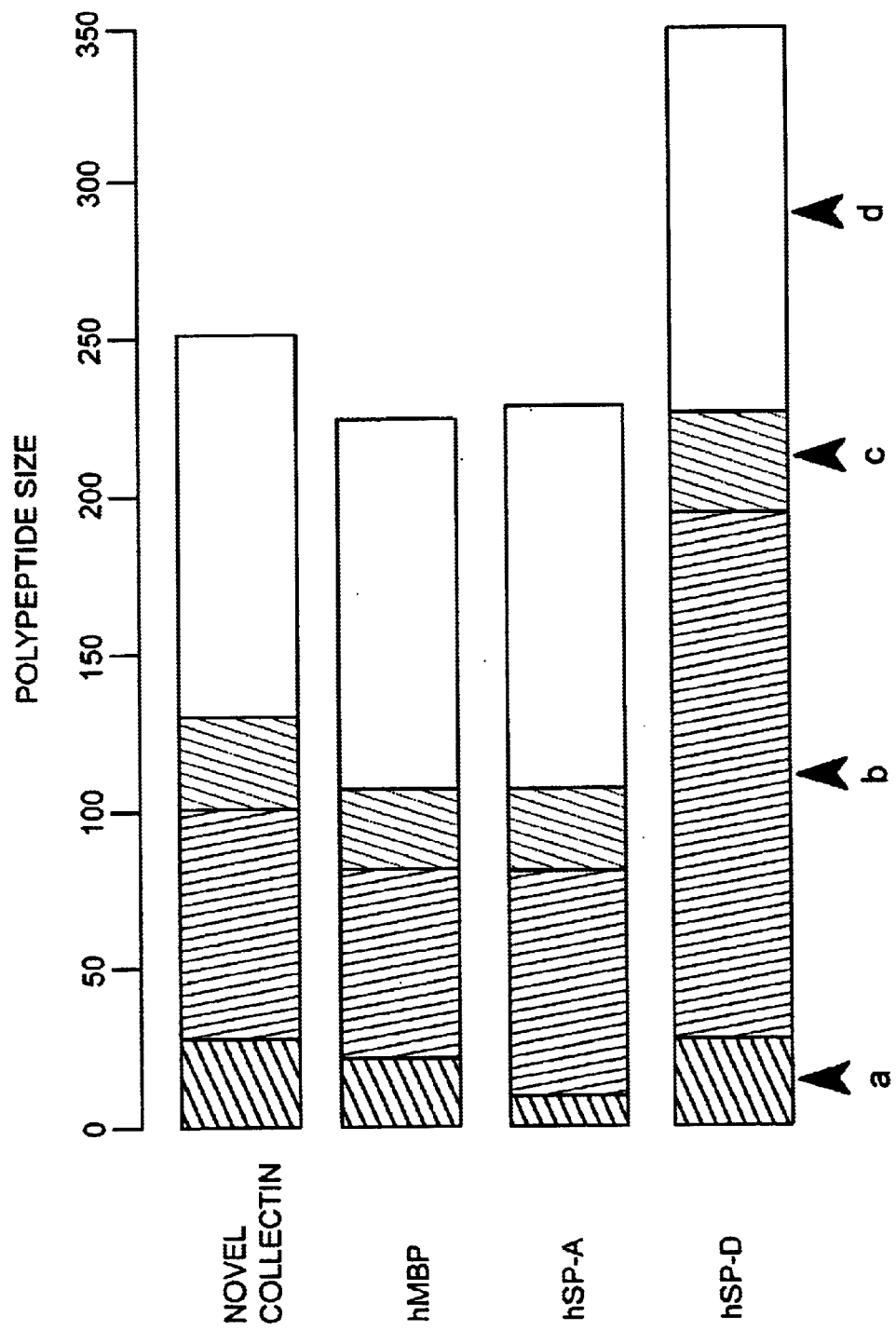
FIG. 7 illustrates a comparison of the basic structures of the three collectins reported heretofore and the novel collectin of the present invention comprising (1) $Ca^{2+}$-dependent carbohydrate recognition domain (CRD), (2)neck region, (3) collagen-like region, and (4) N-terminal region containing cysteine.

Furthermore, under structural studies of the sequence of this novel collectin protein, as shown schematically in FIG. 7, it was suggested that this protein comprised: (a) N-terminal region containing cysteine, (b) as collagen-like region, (c)neck region and (d) carbohydrate recognition domain, as in the case with the known collectins.

However, homology search results on GenBank data base of the DNA and amino acid sequence indicated that the sequence of the obtained protein is distinct from those of the collectins identified previously and it derives from a novel collectin.

EXAMPLE 5

Genomic Southern Analysis of the Novel Collectin

Genomic Southern analysis was performed in order to clarify whether the novel collectin gene comprising the cDNA sequence shown in Example 4 was a single copy gene or a multi copy gene.

Four µg of genomic DNA extracted from placenta was digested with a restriction enzyme, EcoRI, HindIII, BamHI, XbaI or SacI, followed by electrophoresis with 0.7% agarose gel at 100 mA, for 3 hours. After the electrophoresis was completed, the DNA was transferred to a nylon membrane (Nytran 13N) to prepare a membrane for the analysis.

For the transfer step, the electrophoresed gel was immersed in 100 ml of 0.25 N HCl for 10 minutes, washed three times with distilled water, then immersed twice in 100 ml of a denaturalizing solution (1.5 M NaCl, 0.5 M NaOH) for 15 minutes, and immersed in 100 ml of a neutralizing solution (0.5 M Tris-HCl, 3 M NaCl (pH 6.8)) for 30 minutes so that the depurination, denaturalization and neutralization were accomplished. Thereafter, the DNA was transferred using Vacuum Blotting System (Toyobo Engineering, VB-30). In this step, the membrane which had been pretreated by immersing in 2×SSC for 5 minutes and in 20×SSC for 5 minutes was used, with a pad which had been soaked with 20×SSC. After the transfer was terminated, fixation of the DNA was performed by UV irradiation.

Hybridization probe employed for the Southern analysis was the DIG labeled DNA probe corresponding to the cDNA sequence of ORF of the novel collectin as obtained in the above Example 4, which was labeled using the above-described PCR DIG Probe Synthesis Kit. Prior to hybridization, the probe was boiled for 10 minutes, and rapidly frozen with dry ice/ethanol for 5 minutes.

First, the membrane which was subjected to the transfer was immersed in 2×SSC for 5 minutes, then prehybridization was performed in ExpressHyb Hybridization Solution (Clonetech), 10 ml at 68° C. for 30 minutes. Subsequently, the above frozen probe was diluted to 10 ng/ml in ExpressHyb Hybridization Solution and 2 ml of this solution was used for hybridization at 68° C. for one hour.

Following hybridization, the membrane was washed by shaking: two times in 20 ml of 2×SSC, 0.1% SDS at a room temperature for 5 minutes and then two times in 20 ml of 0.2×SSC, 0.1% SDS at 68° C. for 15 minutes. Next, the membrane was washed two, times with 50 ml of DIG buffer I (100 mM Tris-HCl, 150 mM NaCl (pH 7.5)) at a room temperature for one minute in order to remove SDS, and was blocked in DIG buffer II' (1.5% blocking agent in DIG buffer I), 50 ml at a room temperature for one hour. Thereafter, the membrane was treated with 10 ml of alkaline phosphatase labeled anti-DIG antibody which was diluted to 5000-fold in DIG buffer I containing 0.2% Tween20 for 30 minutes followed by washing two times by shaking in 50 ml of DIG buffer I which contains 0.2% Tween20 at a room temperature for 20 minutes. After soaking the membrane twice in 10 ml of DIG buffer III at a room temperature for 3 minutes, it was placed in a hybridization bag, and CSPD (registered trade name, Boehringer Mannheim: chemiluminescence substrate) which was diluted to 100-fold in DIG buffer III was added thereto so that the solution can spread over the membrane. Subsequently, the membrane was exposed to Instant Film 57 (Polaroid).

Figure 8:
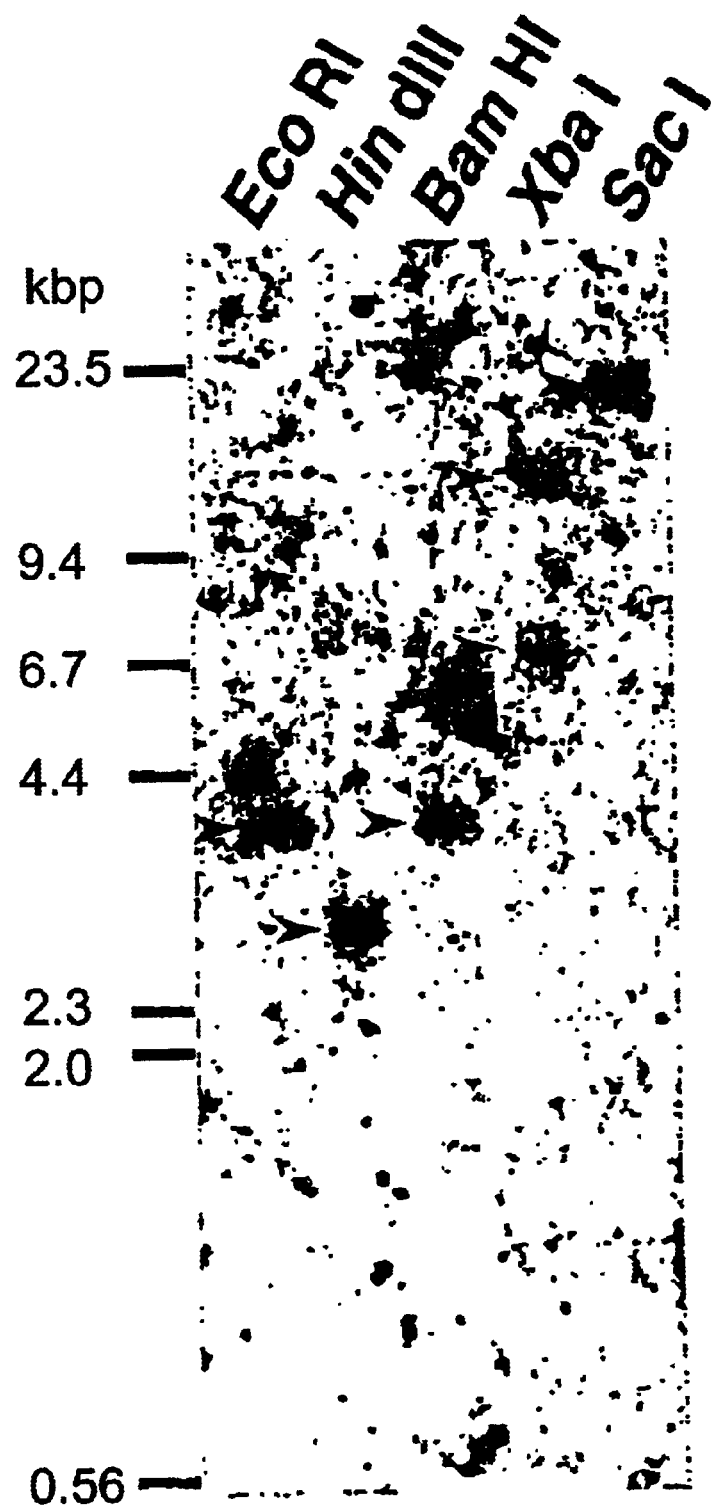
FIG. 8 shows a result of genomic Southern analysis with the novel collectin of the present invention.

Consequently, it was speculated that the gene of the obtained novel collectin has been a single copy gene, because only one or two signals could be detected from the respective genomic DNA which was digested with each of the restriction eves, as shown in the lanes in FIG. 8.

EXAMPLE 6

Northern Analysis of the Novel Collectin with Various Human Tissues

In order to examine the expression of the mRNA of the novel collectin of the present invention in various human tissues, analysis by Northern hybridization was performed.

Hybridization probe employed for this analysis was the DIG labeled RNA probe corresponding to the cDNA sequence of ORF of the novel collectin (SEQ ID NO: 1), which was labeled using DIG RNA Labeling Kit (SP6/T7, Boehringer Mannheim). The analyzed membrane was Human Multiple Tissue Northern (MTN) Blot (Clonetech) containing each poly A$^+$ RNA from human (a) heart, (b) brain, (c) placenta, (d) lung, (e) liver, (f) skeletal muscle, (g) kidney and (h) pancreas, which was prepared by: modification of the electric charge of a nylon membrane prior to transferring the RNA, the RNA transfer from a 1.2% formaldehyde denaturalized agarose gel which had been previously loaded with 2 μg of the above each poly A$^+$ RNA and electrophoresed, and then followed by a fixation using UV irradiation.

Hybridization was carried out using the above-described probe solution and membrane, in accordance with the following procedures. First, the membrane was immersed in 2×SSC for 5 minutes, then prehybridization was performed in 10 ml of hybridization solution (5×SSC, 10× Denhardt's solution, 10 mM sodium phosphate buffer (pH 6.5), 50% formamide, 0.5% SDS, 0.1 mg/ml sermon sperm DNA), at 65° C. for 3 hours. Subsequently, the probe which had previously been boiled for 10 minutes and rapidly frozen with dry ice/ethanol for 5 minutes was diluted in the hybridization solution to be 1 μg/ml, and 2 ml of thus diluted probe solution was used for hybridization at 65° C. for 18 hours.

Following hybridization, the membrane was washed by shaking: two times in 20 ml of 2×SSC, 0.1% SDS at a room temperature for 5 minutes and then two times in 20 ml of 0.1×SSC, 0.1% SDS at 68° C. for 15 minutes. Next, the membrane was washed two times with 50 ml of DIG buffer I at a room temperature for one minute in order to remove SDS, and was blocked in 50 ml of DIG buffer II' at a room temperature for one hour. Thereafter, the membrane was treated with 10 ml of alkaline phosphatase labeled anti-DIG antibody which was diluted to 5000-fold in DIG buffer I which contains 0.2% Tween20 for 30 minutes, followed by washing two times by shaking in 50 ml of DIG buffer I which contains 0.2% Tween20 at a room temperature for 20 minutes. After soaking the membrane twice in 10 ml of DIG buffer III at a room temperature for 3 minutes, it was placed in a hybridization bag, and CSPD which was diluted to 100-fold in DIG buffer III was added thereto so that the solution can spread over the membrane. Subsequently, the membrane was exposed to Instant Film 612 (Polaroid).

Figure 9:
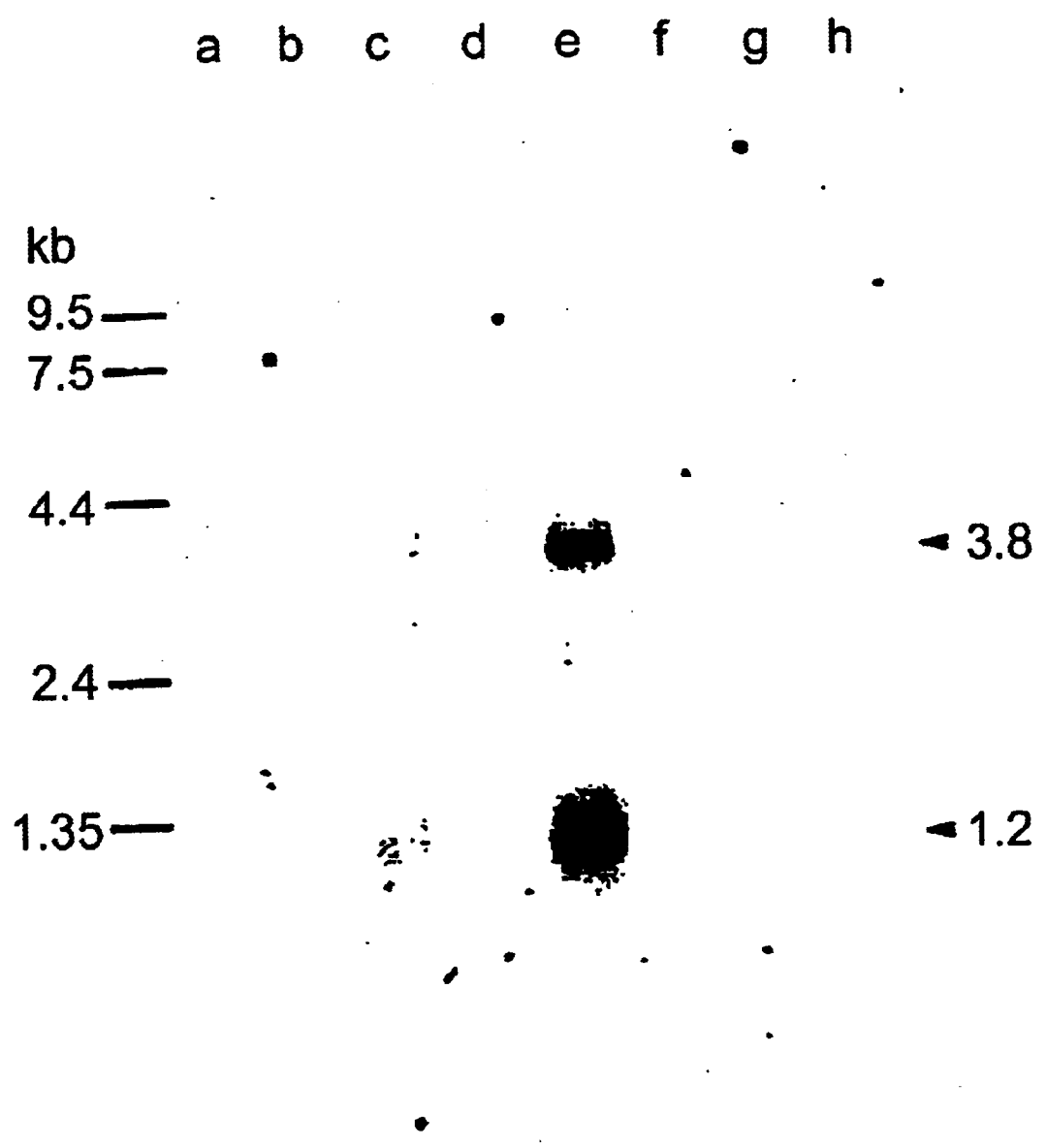

As a consequence, it was revealed that mRNA of the collectin of the present invention having 1.2 kb and 3.8 kb in size has been expressed in liver (lane e) and in placenta (lane c), with more amount being expressed in liver while less but certain amount being expressed in placenta as shown in FIG. 9.

EXAMPLE 7

Genomic Southern Analysis of the Novel Collectin

In order to elucidate conservation of the collectin gene of the present invention between other species of animals, analysis by genomic Southern hybridization was performed.

Hybridization probe employed for this analysis was the DIG labeled DNA probe corresponding to the cDNA sequence of ORF of the novel collectin as obtained in the above Example 4, which was labeled using the above-described PCR DIG Probe Synthesis Kit (Boehringer Mannheim), while the analyzed membrane was ZOO-BLOT (Clonetech). This membrane contains each genomic DNA obtained from (a) human placenta, (b) Rhesus monkey kidney, (c) Sprague-Dawley rat kidney, (d) Balb/c mouse kidney, (e) canine kidney, (f) bovine kidney, (g) rabbit kidney and (h) chicken liver, which was prepared by modification of the electric charge of a nylon membrane prior to transferring the genomic DNA, the DNA transfer from an agarose gel which had been previously loaded with 4 μg of the above each genomic DNA which were digested with restriction enzyme EcoRI, and electrophoresed, then finally followed by a fixation using UV irradiation.

Hybridization was cam ed out using the above-described probe and membrane, in accordance with the following procedures. First, the membrane was immersed in 2×SSC for 5 minutes, then prehybridization was performed in 10 ml of ExpressHyb Hybridization Solution at 65° C. for 30 minutes. Subsequently, the probe which had previously been frozen as described above was diluted in the ExpressHyb Hybridization Solution to be 10 ng/ml, and 2 ml of thus diluted probe solution was used for hybridization at 65° C. for one hour.

Following hybridization, the membrane was washed by shaking: two times in 20 ml of 2×SSC, 0.1% SDS at a room temperature for 5 minutes and then two times in 20 ml of 0.2×SSC, 0.1% SDS at 68° C. for 15 minutes. Next, the membrane was washed two times with DIG buffer I at a room temperature for one minute in order to remove SDS, and was blocked in 50 ml of DIG buffer II' at a room temperature for one hour. Thereafter, the membrane was treated with 10 ml of alkaline phosphatase labeled anti-DIG antibody which was diluted to 5000-fold in DIG buffer I which contains 0.2% Tween20 for 30 minutes followed by washing two times with shaking in 50 ml of DIG buffer I which contains 0.2% Tween20 at a room temperature for 20 minutes. After soaking the membrane twice in 10 ml of DIG buffer III at a room temperature for 3 minutes, it, was placed in a hybridization bag, and CSPD which was diluted to 100-fold in DIG buffer III was added thereto so that the solution can spread over the membrane. Subsequently, the membrane was exposed to Instant Film 57.

Figure 10:
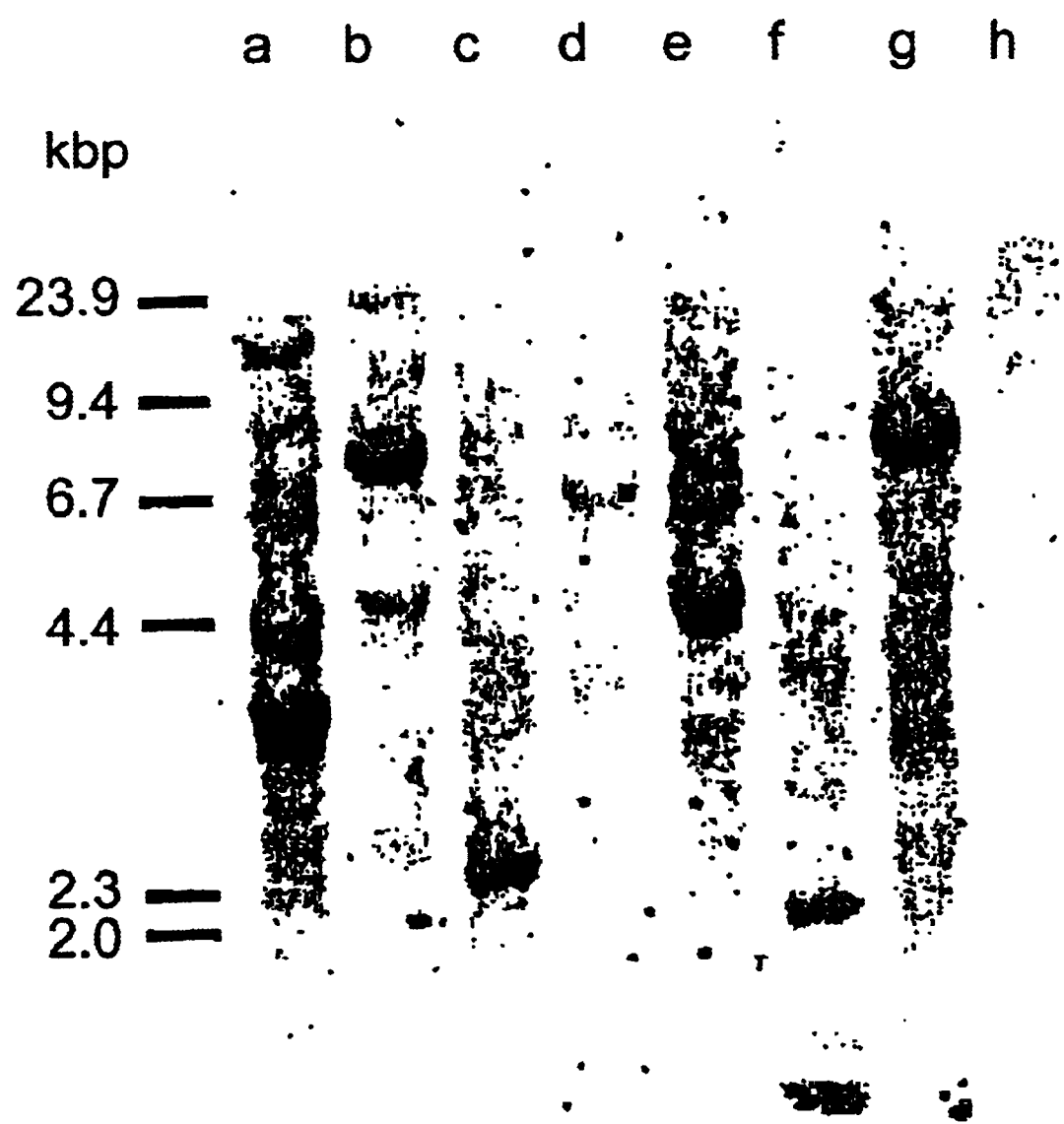
FIG. 10 shows a result of genomic Southern analysis of genes from various vertebrates, i.e., (a) human, (b) monkey, (c) rat, (d) mouse, (e) dog, (f) cow, (g) rabbit and (h) chicken with the novel collectin of the present invention to elucidate the conservation of the collectin during the species.

The result of this analysis is shown in FIG. 10, wherein signals of DNA can been found in all lanes except for the lane h which was loaded with DNA from chicken. Therefore, it was illustrated that the collectin gene of the present invention has been conserved between the mammalian species.

EXAMPLE 8

Genetic Analysis of the Novel Collectin

To elucidate the genetic positional relevance of the present collectin between the known collectins, analysis was performed based on the DNA sequence as obtained, and a phylogenetic tree was created.

The collectins selected as subjects for analysis were: human MBP (Mannan-Binding Protein), human SP-A (Surfactant Protein A), rat MBP-A, rat MBP-C, rat SP-D, mouse MBP-A, mouse MBP-C, rabbit MBP, monkey MBP-A, monkey MBP-C, bovine SP-D, bovine MBP, bovine conglutinin (bKg), and bovine collectin 43 (CL43). Each of the amino acid sequence was retrieved from GenBank data base, then using the regions containing lectin domains from the obtained data, multiple alignment was produced by clustalw method. Thereby, a phylogenetic tree was created using N-J method with Phylip Version 3.57c package program.

Figure 11:
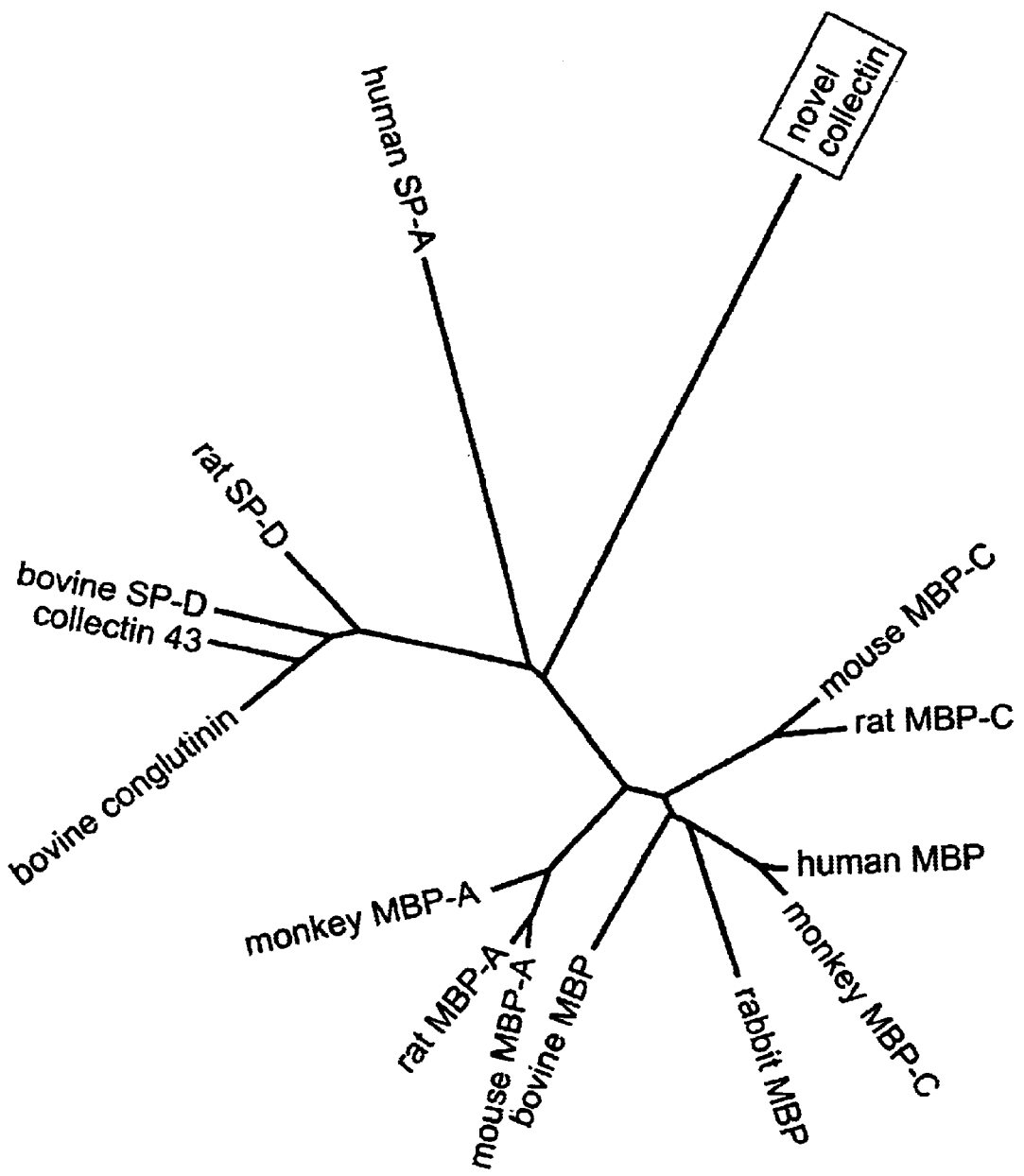
FIG. 11 shows a phylogenetic tree of various collectins.

Consequently, as shown in FIG. 11, although SP-D, bovine collectin 43 and bovine conglutinin have constituted single cluster, additionally MBP and SP-A have respectively constituted separate clusters, while the collectin gene of the present invention has not belonged to any of these clusters. Accordingly, it was speculated that the collectin of the present invention may constitute a distinct cluster which is genetically diverse from those of the collectins reported heretofore.

Industrial Applicability

As set forth above, a novel collectin gene and protein having characteristic structures of the collecting, which are different from the collectins reported so far, are provided by the present invention. Such protein is expected to exhibit physiological activities such as anti-bacterial, anti-viral activity, especially in human body, thereby medicinal applications, as well as tools for investigating mechanisms of biological defense systems may be provided.

What is claimed is:

1. An isolated polynucleotide comprising a nucleotide sequence encoding the amino acid sequence of SEQ ID NO: 2:

Met-Asn-Gly-Phe-Ala-Ser-Leu-Leu-Arg-Arg-Asn-Gln-Phe-Ile-Leu-Leu-Val-Leu-Phe-Leu-Leu-Gln-Ile-Gln-Ser-Leu-Gly-Leu-Asp-Ile-Asp-Ser-Arg-Pro-Thr-Ala-Glu-Val-Cys-Ala-Thr-His-Thr-Ile-Ser-Pro-Gly-Pro-Lys-Gly-Asp-Asp-Gly-Glu-Lys-Gly-Asp-Pro-Gly-Glu-Glu-Gly-Lys-His-Gly-Lys-Val-Gly-Arg-Met-Gly-Pro-Lys-Gly-Ile-Lys-Gly-Glu-Leu-Gly-Asp-Met-Gly-Asp-Arg-Gly-Asn-Ile-Gly-Lys-Thr-Gly-Pro-Ile-Gly-Lys-Lys-Gly-Asp-Lys-Gly-Glu-Lys-Gly-Leu-Leu-Gly-Ile-Pro-Gly-Glu-Lys-Gly-Lys-Ala-Gly-Thr-Val-Cys-Asp-Cys-Gly-Arg-Tyr-Arg-Lys-Phe-Val-Gly-Gln-Leu-Asp-Ile-Ser-Ile-Ala-Arg-Leu-Lys-Thr-Ser-Met-Lys-Phe-Val-Lys-Asn-Val-Ile-Ala-Gly-Ile-Arg-Glu-Thr-Glu-Glu-Lys-Phe-Tyr-Tyr-Ile-Val-Gln-Glu-Glu-Lys-Asn-Tyr-Arg-Glu-Ser-Leu-Thr-His-Cys-Arg-Ile-Arg-Gly-Gly-Met-Leu-Ala-Met-Pro-Lys-Asp-Glu-Ala-Ala-Asn-Thr-Leu-Ile-Ala-Asp-Tyr-Val-Ala-Lys-Ser-Gly-Phe-Phe-Arg-Val-Phe-Ile-Gly-Val-Asn-Asp-Leu-Glu-Arg-Glu-Gly-Gln-Tyr-Met-Phe-Thr-Asp-Asn-Thr-Pro-Leu-Gln-Asn-Tyr-Ser-Asn-Trp-Asn-Glu-Gly-Glu-Pro-Ser-Asp-Pro-Tyr-Gly-His-Glu-Asp-Cys-Val-Glu-Met-Leu-Ser-Ser-Gly-Arg-Trp-Asn-Asp-Thr-Glu-Cys-His-Leu-Thr-Met-Tyr-Phe-Val-Cys-Glu-Phe-Ile-Lys-Lys-Lys-Lys.

2. An isolated polynucleotide consisting of the nucleotide sequence encoding the amino acid sequence of SEQ ID NO: 2:

Met-Asn-Gly-Phe-Ala-Ser-Leu-Leu-Arg-Arg-Asn-Gln-Phe-Ile-Leu-Leu-Val-Leu-Phe-Leu-Leu-Gln-Ile-Gln-Ser-Leu-Gly-Leu-Asp-Ile-Asp-Ser-Arg-Pro-Thr-Ala-Glu-Val-Cys-Ala-Thr-His-Thr-Ile-Ser-Pro-Gly-Pro-Lys-Gly-Asp-Asp-Gly-Glu-Lys-Gly-Asp-Pro-Gly-Glu-Glu-Gly-Lys-His-Gly-Lys-Val-Gly-Arg-Met-Gly-Pro-Lys-Gly-Ile-Lys-Gly-Glu-Leu-Gly-Asp-Met-Gly-Asp-Arg-Gly-Asn-Ile-Gly-Lys-Thr-Gly-Pro-Ile-Gly-Lys-Lys-Gly-Asp-Lys-Gly-Glu-Lys-Gly-Leu-Leu-Gly-Ile-Pro-Gly-Glu-Lys-Gly-Lys-Ala-Gly-Thr-Val-Cys-Asp-Cys-Gly-Arg-Tyr-Arg-Lys-Phe-Val-Gly-Gln-Leu-Asp-Ile-Ser-Ile-Ala-Arg-Leu-Lys-Thr-Ser-Met-Lys-Phe-Val-Lys-Asn-Val-Ile-Ala-Gly-Ile-Arg-Glu-Thr-Glu-Glu-Lys-Phe-Tyr-Tyr-Ile-Val-Gln-Glu-Glu-Lys-Asn-Tyr-Arg-Glu-Ser-Leu-Thr-His-Cys-Arg-Ile-Arg-Gly-Gly-Met-Leu-Ala-Met-Pro-Lys-Asp-Glu-Ala-Ala-Asn-Thr-Leu-Ile-Ala-Asp-Tyr-Val-Ala-Lys-Ser-Gly-Phe-Phe-Arg-Val-Phe-Ile-Gly-Val-Asn-Asp-Leu-Glu-Arg-Glu-Gly-Gln-Tyr-Met-Phe-Thr-Asp-Asn-Thr-Pro-Leu-Gln-Asn-Tyr-Ser-Asn-Trp-Asn-Glu-Gly-Glu-Pro-Ser-Asp-Pro-Tyr-Gly-His-Glu-Asp-Cys-Val-Glu-Met-Leu-Ser-Ser-Gly-Arg-Trp-Asn-Asp-Thr-Glu-Cys-His-Leu-Thr-Met-Tyr-Phe-Val-Cys-Glu-Phe-Ile-Lys-Lys-Lys-Lys.

3. An isolated polynucleotide comprising the nucleotide sequence 6–836 nucleotides of SEQ ID NO: 1:

cagcaatgaa tggctttgca tccttgcttc gaagaaacca atttatcctc ctggtactat ttcttttgca aattcagagt ctgggtctgg atattgatag ccgtcctacc gctgaagtct gtgccacaca cacaatttca ccaggaccca aaggagatga tggtgaaaaa ggagatccag gagaagaggg aaagcatggc aaagtgggac gcatggggcc gaaaggaatt aaaggagaae tgggtgatat gggagatcgg ggcaatattg gcaagactgg gcccattggg aagaagggtg acaaagggga aaaaggtttg cttggaatac ctggagaaaa aggcaaagca ggtactgtct gtgattgtgg aagataccgg aaatttgttg gacaactgga tattagtatt gcccggctca agacatctat gaagtttgtc aagaatgtga tagcagggat tagggaaact gaagagaaat tctactacat cgtgcaggaa gagaagaact acagggaatc cctaacccac tgcaggattc ggggtggaat gctagccatg cccaaggatg aagctgccaa cacactcatc gctgactatg ttgccaagag tggcttcttt cgggtgttca ttggcgtgaa tgaccttgaa agggagggac agtacatgtt cacagacaac actccactgc agaactatag caactggaat gaggggggaac ccagcgaccc ctatggtcat gaggactgtg tggagatgct gagctctggc agatggaatg acacagagtg ccatcttacc atgtactttg tctgtgagtt catcaagaag aaaaagtaac ttccctcatc ctacgtattt gctattttcc tgtgaccgtc attacagtta ttgttatcca tcctttttt cctgattgta ctacatttga tctgagtcaa catagctaga aaatgctaaa ctgaggtatg gagcctccat catcatgctc ttttgtgatg attttcatat tttcacacat ggtatgttat tgacccaata actcgccagg ttacatgggt cttgagagag aattttaatt actaattgtg cacgagatag ttggttgtct atatgtcaaa tgagttgttc tcttggtatt tgctctacca tctctccta gagcactctg tgtctatccc agtggataat ttcccagttt actggtgatg attaggaagg ttgttgatgg ttaggctaac ctgccctggc ccaaagccag acatgtacaa gggctttctg tgagcaatga taagatcttt gaatccaaga tgcccagatg ttttaccagt cacaccctat ggccatggct atacttggaa gttctccttg ttggcacaga catagaaatg ctttaacccc aagcctttat atgggggact tctagctttg tgtcttgttt cagaccatgt ggaatgataa atactctttt tgtgcttctg atctatcgat ttcactaaca tataccaagt aggtgctttg aaccccttc tgtaggctca caccttaatc tcaggcccct atatagtcac actttgattt aagaaaaacg gagcc.

4. An isolated polynucleotide comprising a nucleotide sequence which hybridizes to a non-coding strand complementary to SEQ ID NO: 1 under the following hybridization conditions: hybridization at 55° C. in a hybridization solution comprising 5×SSC, 1% blocking agent, 0.1% N-lauroyl sarcosine and 0.02% SDS; and washing at 55° C. in a wash solution comprising 2×SSC; wherein the polynucleotide encodes a protein having anti-virus activity and comprising: (1) a $Ca^{2+}$-dependent carbohydrate recognition domain (CRD), (2) a neck region, (3) a collagen-like region, and (4) an N-terminal region containing cysteine.

5. The polynucleotide according to claim 1 wherein said polynucleotide is cDNA.

6. The polynucleotide according to claim 2 wherein said polynucleotide is cDNA.

7. An isolated collectin protein comprising the amino acid sequence of SEQ ID NO: 2:

Met-Asn-Gly-Phe-Ala-Ser-Leu-Leu-Arg-Arg-Asn-Gln-Phe-Ile-Leu-Leu-Val-Leu-Phe-Leu-Leu-Gln-Ile-Gln-Ser-Leu-Gly-Leu-Asp-Ile-Asp-Ser-Arg-Pro-Thr-Ala-Glu-Val-Cys-Ala-Thr-His-Thr-Ile-Ser-Pro-Gly-Pro-Lys-Gly-Asp-Asp-Gly-Glu-Lys-Gly-Asp-Pro-Gly-Glu-Glu-Gly-Lys-His-Gly-Lys-Val-Gly-Arg-Met-Gly-Pro-Lys-Gly-Ile-Lys-Gly-Glu-Leu-Gly-Asp-Met-Gly-Asp-Arg-Gly-Asn-Ile-Gly-Lys-Thr-Gly-Pro-Ile-Gly-Lys-Lys-Gly-Asp-Lys-Gly-Glu-Lys-Gly-Leu-Leu-Gly-Ile-Pro-Gly-Glu-Lys-Gly-Lys-Ala-Gly-Thr-Val-Cys-Asp-Cys-Gly-Arg-Tyr-Arg-Lys-Phe-Val-Gly-Gln-Leu-Asp-Ile-Ser-Ile-Ala-Arg-Leu-Lys-Thr-Ser-Met-Lys-Phe-Val-Lys-Asn-Val-Ile-Ala-Gly-Ile-Arg-Glu-Thr-Glu-Glu-Lys-Phe-Tyr-Tyr-Ile-Val-Gln-Glu-Glu-Lys-Asn-Tyr-Arg-Glu-Ser-Leu-Thr-His-Cys-Arg-Ile-Arg-Gly-Gly-Met-Leu-Ala-Met-Pro-Lys-Asp-Glu-Ala-Ala-Asn-Thr-Leu-Ile-Ala-Asp-Tyr-Val-Ala-Lys-Ser-Gly-Phe-Phe-Arg-Val-Phe-Ile-Gly-Val-Asn-Asp-Leu-Glu-Arg-Glu-Gly-Gln-Tyr-Met-Phe-Thr-Asp-Asn-Thr-Pro-Leu-Gln-Asn-Tyr-Ser-Asn-Trp-Asn-Glu-Gly-Glu-Pro-Ser-Asp-Pro-Tyr-Gly-His-Glu-Asp-Cys-Val-Glu-Met-Leu-Ser-Ser-Gly-Arg-Trp-Asn-Asp-Thr-Glu-Cys-His-Leu-Thr-Met-Tyr-Phe-Val-Cys-Glu-Phe-Ile-Lys-Lys-Lys-Lys.

8. An isolated collectin protein consisting of the amino acid sequence of SEQ ID NO: 2:

Met-Asn-Gly-Phe-Ala-Ser-Leu-Leu-Arg-Arg-Asn-Gln-Phe-Ile-Leu-Leu-Val-Leu-Phe-Leu-Leu-Gln-Ile-Gln-Ser-Leu-Gly-Leu-Asp-Ile-Asp-Ser-Arg-Pro-Thr-Ala-Glu-Val-Cys-Ala-Thr-His-Thr-Ile-Ser-Pro-Gly-Pro-Lys-Gly-Asp-Asp-Gly-Glu-Lys-Gly-Asp-Pro-Gly-Glu-Glu-Gly-Lys-His-Gly-Lys-Val-Gly-Arg-Met-Gly-Pro-Lys-Gly-Ile-Lys-Gly-Glu-Leu-Gly-Asp-Met-Gly-Asp-Arg-Gly-Asn-Ile-Gly-Lys-Thr-Gly-Pro-Ile-Gly-Lys-Lys-Gly-Asp-Lys-Gly-Glu-Lys-Gly-Leu-Leu-Gly-Ile-Pro-Gly-Glu-Lys-Gly-Lys-Ala-Gly-Thr-Val-Cys-Asp-Cys-Gly-Arg-Tyr-Arg-Lys-Phe-Val-Gly-Gln-Leu-Asp-Ile-Ser-Ile-Ala-Arg-Leu-Lys-Thr-Ser-Met-Lys-Phe-Val-Lys-Asn-Val-Ile-Ala-Gly-Ile-Arg-Glu-Thr-Glu-Glu-Lys-Phe-Tyr-Tyr-Ile-Val-Gln-Glu-Glu-Lys-Asn-Tyr-Arg-Glu-Ser-Leu-Thr-His-Cys-Arg-Ile-Arg-Gly-Gly-Met-Leu-Ala-Met-Pro-Lys-Asp-Glu-Ala-Ala-Asn-Thr-Leu-Ile-Ala-Asp-Tyr-Val-Ala-Lys-Ser-Gly-Phe-Phe-Arg-Val-Phe-Ile-Gly-Val-Asn-Asp-Leu-Glu-Arg-Glu-Gly-Gln-Tyr-Met-Phe-Thr-Asp-Asn-Thr-Pro-Leu-Gln-Asn-Tyr-Ser-Asn-Trp-Asn-Glu-Gly-Glu-Pro-Ser-Asp-Pro-Tyr-Gly-His-Glu-Asp-Cys-Val-Glu-Met-Leu-Ser-Ser-Gly-Arg-Trp-Asn-Asp-Thr-Glu-Cys-His-Leu-Thr-Met-Tyr-Phe-Val-Cys-Glu-Phe-Ile-Lys-Lys-Lys-Lys.

9. An isolated collectin protein consisting of the amino acid sequence encoded by the nucleotide sequence 6–836 nucleotides of SEQ ID NO: 1:

cagcaatgaa tggctttgca tccttgcttc gaagaaacca atttatcctc ctg-gtactat ttcttttgca aattcagagt ctgggtctgg atattgatag ccgtc-ctacc gctgaagtct gtgccacaca cacaatttca ccaggaccca aag-gagatga tggtgaaaaa ggagatccag gagaagaggg aaagcatggc aaagtgggac gcatggggcc gaaaggaatt aaaggagaac tgggt-gatat gggagatcgg ggcaatattg gcaagactgg gcccattggg aagaagggtg acaagggga aaaaggtttg cttggaatac ctg-gagaaaa aggcaaagca ggtactgtct gtgattgtgg aagataccgg aaatttgttg gacaactgga tattagtatt gcccggctca agacatctat gaagtttgtc aagaatgtga tagcagggat tagggaaact gaa-gagaaat tctactacat cgtgcaggaa gagaagaact acagggaatc cctaacccac tgcaggattc ggggtggaat gctagccatg cccaag-gatg aagctgccaa cacactcatc gctgactatg ttgccaagag tggct-tcttt cgggtgttca ttggcgtgaa tgaccttgaa agggagggac agta-catgtt cacagacaac actccactgc agaactatag caactggaat gagggggaac ccagcgaccc ctatggtcat gaggactgtg tggagat-gct gagctctggc agatggaatg acacagagtg ccatcttacc atg-tactttg tctgtgagtt catcaagaag aaaaagtaac ttccctcatc ctacgtattt gctatttcc tgtgaccgtc attacagtta ttgttatcca tccttttttt cctgattgta ctacatttga tctgagtcaa catagctaga aaatgctaaa ctgaggtatg gagcctccat catcatgctc ttttgtgatg attttcatat tttcacacat ggtatgttat tgacccaata actcgccagg tta-catgggt cttgagagag aattttaatt actaattgtg cacgagatag ttg-gttgtct atatgtcaaa tgagttgttc tcttggtatt tgctctacca tctctc-ccta gagcactctg tgtctatccc agtggataat ttcccagttt actggtgatg attaggaagg ttgttgatgg ttaggctaac ctgccctggc ccaaagccag acatgtacaa gggctttctg tgagcaatga taagatcttt gaatccaaga tgcccagatg ttttaccagt cacaccctat ggccatggct atacttggaa gttctccttg ttggcacaga catagaaatg ctttaacccc aagcctttat atgggggact tctagcttg tgtcttgttt cagaccatgt ggaatgataa atactctttt tgtgcttctg atctatcgat ttcactaaca tataccaagt aggtgctttg aaccccttc tgtaggctca caccttaatc tcaggcccct atatagtcac acttgattt aagaaaaacg gagcc.

10. The isolated collectin protein according to claim 7 or 9, wherein the protein comprises: (1) the $Ca^{2+}$-dependent carbohydrate recognition domain comprising amino acid 1 to 46 of SEQ ID NO: 2, (2) the neck region comprising amino acid 47 to 118 of SEQ ID NO: 2, (3) the collagen-like region comprising amino acid 119 to 147 of SEQ ID NO: 2, and (4) the N-terminal region containing cysteine comprising amino acid 148 to 227 of SEQ ID NO: 2.

11. A method for isolating a polynucleotide encoding the collectin protein according to claim 7 or 9 comprising the steps of:

(i) preparing a probe which is complementary to the nucleotide sequence of SEQ ID NO: 1;

(ii) hybridizing the probe with a candidate polynucleotide at 55° C. in a hybridization solution comprising 5×SSC, 1% blocking agent, 0.1% N-Lauroyl sarcosine and 0.02% SDS;

(iii) washing the unhybridized probe at 55° C. in a wash solution comprising 2×SSC;

and (iv) isolating the hybridized polynucleotide.

12. An isolated polynucleotide, which is complementary to the isolated polynucleotide of claim 4.

13. An isolated collectin protein comprising the amino acid sequence of SEQ ID NO: 2 wherein said amino acid sequence further comprises deletion, substitution and/or addition of(1) one to ten amino acid residue(s) in the $Ca^{2+}$-dependent carbohydrate recognition domain, amino acids 1 to 46 of SEQ ID NO: 2, (2) one to ten amino acid residue(s) in the neck region, amino acids 47 to 118 of SEQ ID NO: 2, (3) one to fifteen amino acid residue(s) in the collagen-like region comprises amino acids 119 to 147 of SEQ ID NO: 2, and (4) one to twenty amino acid residue(s) in the N-terminal region containing cysteine comprises amino acids 148 to 227 of SEQ ID NO: 2, wherein said collectin protein has anti-virus activity.

* * * * *

UNITED STATES PATENT AND TRADEMARK OFFICE
CERTIFICATE OF CORRECTION

| | | |
|---|---|---|
| PATENT NO. | : 6,787,639 B1 | Page 1 of 1 |
| APPLICATION NO. | : 09/600932 | |
| DATED | : September 7, 2004 | |
| INVENTOR(S) | : Nobutaka Wakamiya | |

It is certified that error appears in the above-identified patent and that said Letters Patent is hereby corrected as shown below:

Column 31, line 25, please delete "lie" and insert --Ile--.

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 29

<210> SEQ ID NO 1
<211> LENGTH: 1595
<212> TYPE: DNA
<213> ORGANISM: Homo sapiens
<220> FEATURE:
<221> NAME/KEY: CDS
<222> LOCATION: (6)..(836)

<400> SEQUENCE: 1 cagca atg aat ggc ttt gca tcc ttg ctt cga aga aac caa ttt atc ctc       50
      Met Asn Gly Phe Ala Ser Leu Leu Arg Arg Asn Gln Phe Ile Leu
        1               5                  10                  15 ctg gta cta ttt ctt ttg caa att cag agt ctg ggt ctg gat att gat         98
Leu Val Leu Phe Leu Leu Gln Ile Gln Ser Leu Gly Leu Asp Ile Asp
                20                  25                  30 agc cgt cct acc gct gaa gtc tgt gcc aca cac aca att tca cca gga        146
Ser Arg Pro Thr Ala Glu Val Cys Ala Thr His Thr Ile Ser Pro Gly
            35                  40                  45 ccc aaa gga gat gat ggt gaa aaa gga gat cca gga gaa gag gga aag        194
Pro Lys Gly Asp Asp Gly Glu Lys Gly Asp Pro Gly Glu Glu Gly Lys
        50                  55                  60 cat ggc aaa gtg gga cgc atg ggg ccg aaa gga att aaa gga gaa ctg        242
His Gly Lys Val Gly Arg Met Gly Pro Lys Gly Ile Lys Gly Glu Leu
    65                  70                  75 ggt gat atg gga gat cgg ggc aat att ggc aag act ggg ccc att ggg        290
```

| | | |
|---|---|---|
| Gly Asp Met Gly Asp Arg Gly Asn Ile Gly Lys Thr Gly Pro Ile Gly<br>80                                85                            90                              95 | |

```
aag aag ggt gac aaa ggg gaa aaa ggt ttg ctt gga ata cct gga gaa        338
Lys Lys Gly Asp Lys Gly Glu Lys Gly Leu Leu Gly Ile Pro Gly Glu
            100                 105                 110 aaa ggc aaa gca ggt act gtc tgt gat tgt gga aga tac cgg aaa ttt        386
Lys Gly Lys Ala Gly Thr Val Cys Asp Cys Gly Arg Tyr Arg Lys Phe
        115                 120                 125 gtt gga caa ctg gat att agt att gcc cgg ctc aag aca tct atg aag        434
Val Gly Gln Leu Asp Ile Ser Ile Ala Arg Leu Lys Thr Ser Met Lys
    130                 135                 140 ttt gtc aag aat gtg ata gca ggg att agg gaa act gaa gag aaa ttc        482
Phe Val Lys Asn Val Ile Ala Gly Ile Arg Glu Thr Glu Glu Lys Phe
145                 150                 155 tac tac atc gtg cag gaa gag aag aac tac agg gaa tcc cta acc cac        530
Tyr Tyr Ile Val Gln Glu Glu Lys Asn Tyr Arg Glu Ser Leu Thr His
160                 165                 170                 175 tgc agg att cgg ggt gga atg cta gcc atg ccc aag gat gaa gct gcc        578
Cys Arg Ile Arg Gly Gly Met Leu Ala Met Pro Lys Asp Glu Ala Ala
                180                 185                 190 aac aca ctc atc gct gac tat gtt gcc aag agt ggc ttc ttt cgg gtg        626
Asn Thr Leu Ile Ala Asp Tyr Val Ala Lys Ser Gly Phe Phe Arg Val
            195                 200                 205 ttc att ggc gtg aat gac ctt gaa agg gag gga cag tac atg ttc aca        674
Phe Ile Gly Val Asn Asp Leu Glu Arg Glu Gly Gln Tyr Met Phe Thr
        210                 215                 220 gac aac act cca ctg cag aac tat agc aac tgg aat gag ggg gaa ccc        722
Asp Asn Thr Pro Leu Gln Asn Tyr Ser Asn Trp Asn Glu Gly Glu Pro
    225                 230                 235 agc gac ccc tat ggt cat gag gac tgt gtg gag atg ctg agc tct ggc        770
Ser Asp Pro Tyr Gly His Glu Asp Cys Val Glu Met Leu Ser Ser Gly
240                 245                 250                 255 aga tgg aat gac aca gag tgc cat ctt acc atg tac ttt gtc tgt gag        818
Arg Trp Asn Asp Thr Glu Cys His Leu Thr Met Tyr Phe Val Cys Glu
                260                 265                 270 ttc atc aag aag aaa aag taacttccct catcctacgt atttgctatt              866
Phe Ile Lys Lys Lys Lys
                275 ttcctgtgac cgtcattaca gttattgtta tccatccttt ttttcctgat tgtactacat     926 ttgatctgag tcaacatagc tagaaaatgc taaactgagg tatggagcct ccatcatcat     986 gctcttttgt gatgattttc atattttcac acatggtatg ttattgaccc ataactcgc    1046 caggttacat gggtcttgag agagaatttt aattactaat tgtgcacgag atagttggtt   1106 gtctatatgt caaatgagtt gttctcttgg tatttgctct accatctctc cctagagcac   1166 tctgtgtcta tcccagtgga taatttccca gtttactggt gatgattagg aaggttgttg   1226 atggttaggc taacctgccc tggcccaaag ccagacatgt acaagggctt tctgtgagca   1286 atgataagat ctttgaatcc aagatgccca gatgttttac cagtcacacc ctatggccat   1346 ggctatactt ggaagttctc cttgttggca cagacataga aatgctttaa ccccaagcct   1406 ttatatgggg gacttctagc tttgtgtctt gtttcagacc atgtggaatg ataaatactc   1466 tttttgtgct tctgatctat cgatttcact aacatatacc aagtaggtgc tttgaacccc   1526 tttctgtagg ctcacacctt aatctcaggc ccctatatag tcacactttg atttaagaaa   1586 aacggagcc                                                          1595
```

<210> SEQ ID NO 2

<211> LENGTH: 277
<212> TYPE: PRT
<213> ORGANISM: Homo sapiens

<400> SEQUENCE: 2

Met Asn Gly Phe Ala Ser Leu Leu Arg Arg Asn Gln Phe Ile Leu Leu
 1               5                  10                  15
Val Leu Phe Leu Leu Gln Ile Gln Ser Leu Gly Leu Asp Ile Asp Ser
            20                  25                  30
Arg Pro Thr Ala Glu Val Cys Ala Thr His Thr Ile Ser Pro Gly Pro
        35                  40                  45
Lys Gly Asp Asp Gly Glu Lys Gly Asp Pro Gly Glu Glu Gly Lys His
    50                  55                  60
Gly Lys Val Gly Arg Met Gly Pro Lys Gly Ile Lys Gly Glu Leu Gly
65                  70                  75                  80
Asp Met Gly Asp Arg Gly Asn Ile Gly Lys Thr Gly Pro Ile Gly Lys
                85                  90                  95
Lys Gly Asp Lys Gly Glu Lys Gly Leu Leu Gly Ile Pro Gly Glu Lys
            100                 105                 110
Gly Lys Ala Gly Thr Val Cys Asp Cys Gly Arg Tyr Arg Lys Phe Val
        115                 120                 125
Gly Gln Leu Asp Ile Ser Ile Ala Arg Leu Lys Thr Ser Met Lys Phe
    130                 135                 140
Val Lys Asn Val Ile Ala Gly Ile Arg Glu Thr Glu Lys Phe Tyr
145                 150                 155                 160
Tyr Ile Val Gln Glu Glu Lys Asn Tyr Arg Glu Ser Leu Thr His Cys
                165                 170                 175
Arg Ile Arg Gly Gly Met Leu Ala Met Pro Lys Asp Glu Ala Ala Asn
            180                 185                 190
Thr Leu Ile Ala Asp Tyr Val Ala Lys Ser Gly Phe Phe Arg Val Phe
        195                 200                 205
Ile Gly Val Asn Asp Leu Glu Arg Glu Gly Gln Tyr Met Phe Thr Asp
    210                 215                 220
Asn Thr Pro Leu Gln Asn Tyr Ser Asn Trp Asn Glu Gly Glu Pro Ser
225                 230                 235                 240
Asp Pro Tyr Gly His Glu Asp Cys Val Glu Met Leu Ser Ser Gly Arg
                245                 250                 255
Trp Asn Asp Thr Glu Cys His Leu Thr Met Tyr Phe Val Cys Glu Phe
            260                 265                 270
Ile Lys Lys Lys Lys
        275

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Consensus
      sequence of collectins which were reported
      heretofore

<400> SEQUENCE: 3

Glu Lys Cys Val Glu Met Tyr Thr Asp Gly Lys Trp Asn Asp Arg Asn
 1               5                  10                  15
Cys Leu Gln Ser Arg Leu Ala Ile Cys Glu Phe
            20                  25

```
<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Pre-
      sequence of an Insert

<400> SEQUENCE: 4
gaattcggca cgag                                                    14

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: M13
      Universal Primer Sequence for Sequencing

<400> SEQUENCE: 5
cgacgttgta aaacgacggc cagt                                         24

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: M13 Reverse
      Primer Sequence for Sequencing

<400> SEQUENCE: 6
caggaaacag ctatgac                                                 17

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Sequence of
      a Reverse Primer for Screening a Novel Collectin

<400> SEQUENCE: 7
ttttgatgga ggctccatac c                                            21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Sequence of
      a Forward Primer for Screening a Novel Collectin

<400> SEQUENCE: 8
ctgccaacac actcatcgct g                                            21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Sequence of
      a lambda gt11 Reverse Primer for Sequencing

<400> SEQUENCE: 9
ttgacaccag accaactggt aatg                                         24

<210> SEQ ID NO 10
```

-continued

```
<211> LENGTH: 24
<212> TYPE: DNA
<213> ORGANISM: Artificial Sequence
<220> FEATURE:
<223> OTHER INFORMATION: Description of Artificial Sequence: Sequence of
      a lambda gt11 Forward Primer for Sequencing

<400> SEQUENCE: 10
ggtggcgacg actcctggag cccg                                              24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 11
taatggtagc gaccggcgct                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 12
aaaccaattt atactcctgg                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 13
aatattggca agactgggcc                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 14
gatgagtgtg ttggcagcat                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 15
gtatcttcca caatcacaga                                                   20

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 16
ttaattcctt tcggccccat                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 17
gcaaaagaaa tagtaccagg                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 18
catatcaccc agttctcctt                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 19
agcagggatt agggaaactg                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 20
ctgtgagcgt cattacagtt                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 21
ggttgtctat atgtcaaatg                                                  20

<210> SEQ ID NO 22
<211> LENGTH: 20
<212> TYPE: DNA
```

```
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 22
tatggccatg gctatacttg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 23
atcgctgact atgttgccaa                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 24
caagtatagc catggccata                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 25
aactgtaatg acgctcacag                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Sequence of
      a Synthetic Primer for Sequencing a Novel Collectin

<400> SEQUENCE: 26
catttgacat atgaacaacc                                                    20

<210> SEQ ID NO 27
<211> LENGTH: 248
<212> TYPE: PRT
<213> ORGANISM: Homo sapiens
<220> FEATURE:
<223> OTHER INFORMATION: mannan-binding protein (MBP)

<400> SEQUENCE: 27

Met Ser Leu Phe Pro Ser Leu Pro Leu Leu Leu Leu Ser Met Val Ala
  1               5                  10                  15

Ala Ser Tyr Ser Glu Thr Val Thr Cys Glu Asp Ala Gln Lys Thr Cys
             20                  25                  30

Pro Ala Val Ile Ala Cys Ser Ser Pro Gly Ile Asn Gly Phe Pro Gly
         35                  40                  45
```

-continued

```
Lys Asp Gly Arg Asp Gly Thr Lys Gly Glu Lys Gly Glu Pro Gly Gln
 50                  55                  60
Gly Leu Arg Gly Leu Gln Gly Pro Pro Gly Lys Leu Gly Pro Pro Gly
 65                  70                  75                  80
Asn Pro Gly Pro Ser Gly Ser Pro Gly Pro Lys Gly Gln Lys Gly Asp
                 85                  90                  95
Pro Gly Lys Ser Pro Asp Gly Asp Ser Ser Leu Ala Ala Ser Glu Arg
                100                 105                 110
Lys Ala Leu Gln Thr Glu Met Ala Arg Ile Lys Lys Trp Leu Thr Phe
            115                 120                 125
Ser Leu Gly Lys Gln Val Gly Asn Lys Phe Phe Leu Thr Asn Gly Glu
        130                 135                 140
Ile Met Thr Phe Glu Lys Val Lys Ala Leu Cys Val Lys Phe Gln Ala
145                 150                 155                 160
Ser Val Ala Thr Pro Arg Asn Ala Ala Glu Asn Gly Ala Ile Gln Asn
                165                 170                 175
Leu Ile Lys Glu Glu Ala Phe Leu Gly Ile Thr Asp Glu Lys Thr Glu
            180                 185                 190
Gly Gln Phe Val Asp Leu Thr Gly Asn Arg Leu Thr Tyr Thr Asn Trp
        195                 200                 205
Asn Glu Gly Glu Pro Asn Asn Ala Gly Ser Asp Glu Asp Cys Val Leu
210                 215                 220
Leu Leu Lys Asn Gly Gln Trp Asn Asp Val Pro Cys Ser Thr Ser His
225                 230                 235                 240
Leu Ala Val Cys Glu Phe Pro Ile
                245

<210> SEQ ID NO 28
<211> LENGTH: 248
<212> TYPE: PRT
<213> ORGANISM: Homo sapiens
<220> FEATURE:
<223> OTHER INFORMATION: surfactant protein A (SP-A)

<400> SEQUENCE: 28

Met Trp Leu Cys Pro Leu Ala Leu Thr Leu Ile Leu Met Ala Ala Ser
 1               5                  10                  15
Gly Ala Ala Cys Glu Val Lys Asp Val Cys Val Gly Ser Pro Gly Ile
                 20                  25                  30
Pro Gly Thr Pro Gly Ser His Gly Leu Pro Gly Arg Asp Gly Arg Asp
             35                  40                  45
Gly Val Lys Gly Asp Pro Gly Pro Pro Gly Pro Met Gly Pro Pro Gly
 50                  55                  60
Glu Thr Pro Cys Pro Pro Gly Asn Asn Gly Leu Pro Gly Ala Pro Gly
 65                  70                  75                  80
Val Pro Gly Glu Arg Gly Glu Lys Gly Glu Pro Gly Glu Arg Gly Pro
                 85                  90                  95
Pro Gly Leu Pro Ala His Leu Asp Glu Glu Leu Gln Ala Thr Leu His
            100                 105                 110
Asp Phe Arg His Gln Ile Leu Gln Thr Arg Gly Ala Leu Ser Leu Gln
        115                 120                 125
Gly Ser Ile Met Thr Val Gly Glu Lys Val Phe Ser Ser Asn Gly Gln
    130                 135                 140
Ser Ile Thr Phe Asp Ala Ile Gln Glu Ala Cys Ala Arg Ala Gly Gly
145                 150                 155                 160
```

```
Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 29
<211> LENGTH: 375
<212> TYPE: PRT
<213> ORGANISM: Homo sapiens
<220> FEATURE:
<223> OTHER INFORMATION: surfactant protein D (SP-D)

<400> SEQUENCE: 29

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Ala Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270
```

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
        290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350

Glu Ile Phe Thr Asn Gly Lys Trp Asn Asp Arg Ala Cys Gly Glu Lys
        355                 360                 365

Arg Leu Val Val Cys Glu Phe
    370                 375